US012812078B2

(12) United States Patent
Sidar et al.

(10) Patent No.: US 12,812,078 B2
(45) **Date of Patent: *Nov. 24, 2026**

(54) ENDOSCOPIC IMAGE ENHANCEMENT USING CONTRAST LIMITED ADAPTIVE HISTOGRAM EQUALIZATION (CLAHE) IMPLEMENTED IN A PROCESSOR

(71) Applicant: EndoChoice, Inc., Alpharetta, GA (US)

(72) Inventors: Itay Sidar, Haifa (IL); Tal Davidson, Yokneam Ilit (IL); Achia Kronman, Pardes Hana (IL); Lior Mor, Haifa (IL); Idan Levy, Hadera (IL)

(73) Assignee: EndoChoice, Inc., Alpharetta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/019,836

(22) Filed: Jan. 14, 2025

(65) Prior Publication Data

US 2025/0159121 A1 May 15, 2025

Related U.S. Application Data

(63) Continuation of application No. 18/353,271, filed on Jul. 17, 2023, now Pat. No. 12,231,829, which is a (Continued)

(51) Int. Cl.

| | |
|---|---|
| ***H04N 9/64*** | (2023.01) |
| ***A61B 1/00*** | (2006.01) |
| ***G06T 5/20*** | (2006.01) |
| ***G06T 5/40*** | (2006.01) |
| ***G06T 5/92*** | (2024.01) |

(52) U.S. Cl.

CPC ....... *H04N 9/646* (2013.01); *A61B 1/000095* (2022.02); *G06T 5/20* (2013.01); *G06T 5/40* (2013.01); *G06T 5/92* (2024.01); *A61B 1/0005* (2013.01); *G06T 2200/28* (2013.01)

(58) Field of Classification Search

CPC .... H04N 9/64; A61B 1/00; G06T 5/20; G06T 5/40

See application file for complete search history.

(56) References Cited

U.S. PATENT DOCUMENTS

| | | | |
|---|---|---|---|
| 4,027,697 | A | 6/1977 | Bonney |
| 4,084,401 | A | 4/1978 | Belardi |

(Continued)

FOREIGN PATENT DOCUMENTS

| | | |
|---|---|---|
| CA | 2297986 | 3/1999 |
| CA | 2765559 | 12/2010 |

(Continued)

OTHER PUBLICATIONS

YUV YCbCr YPbPr color spaces; 2010. (Year: 2010).*

(Continued)

*Primary Examiner* — Luis Perez-Fuentes

(74) *Attorney, Agent, or Firm* — Bookoff McAndrews PLLC

(57) ABSTRACT

Systems and methods of enhancing images use a contrast limited adaptive histogram equalization (CLAHE) algorithm in a field programmable gate array (FPGA). The images may be obtained by the imaging elements of a multiple imaging elements endoscope of an endoscopy system.

20 Claims, 13 Drawing Sheets

Related U.S. Application Data continuation of application No. 17/658,689, filed on Apr. 11, 2022, now Pat. No. 11,750,782, which is a continuation of application No. 16/992,312, filed on Aug. 13, 2020, now Pat. No. 11,330,238, which is a continuation of application No. 16/685,299, filed on Nov. 15, 2019, now Pat. No. 10,791,308, which is a continuation of application No. 15/155,814, filed on May 16, 2016, now Pat. No. 10,516,865.

(60) Provisional application No. 62/259,683, filed on Nov. 25, 2015, provisional application No. 62/162,788, filed on May 17, 2015.

(56) References Cited

U.S. PATENT DOCUMENTS 4,402,313 A 9/1983 Yabe
4,461,282 A 7/1984 Ouch
4,494,549 A 1/1985 Namba
4,532,918 A 8/1985 Wheeler
4,588,294 A 5/1986 Siegmund
4,641,635 A 2/1987 Yabe
4,727,859 A 3/1988 Lia
4,764,001 A 8/1988 Yokota
4,801,792 A 1/1989 Yamasita
4,825,850 A 5/1989 Opie
4,877,314 A 10/1989 Kanamori
4,902,115 A 2/1990 Takahashi
4,976,522 A 12/1990 Igarashi
4,984,878 A 1/1991 Miyano
5,007,406 A 4/1991 Takahashi
5,014,685 A 5/1991 Takahashi
5,193,525 A 3/1993 Silverstein
5,224,929 A 7/1993 Remiszewski
5,296,971 A 3/1994 Mori
5,359,456 A 10/1994 Kikuchi
5,395,329 A 3/1995 Fleischhacker
5,447,148 A 9/1995 Oneda
5,460,167 A 10/1995 Yabe
5,464,007 A 11/1995 Krauter
5,489,266 A 2/1996 Adair
5,518,501 A 5/1996 Oneda
5,518,502 A 5/1996 Kaplan
5,547,457 A 8/1996 Tsuyuki
5,575,755 A 11/1996 Krauter
5,587,839 A 12/1996 Miyano
5,630,782 A 5/1997 Adair
5,662,588 A 9/1997 Lida
5,674,182 A 10/1997 Suzuki
5,685,823 A 11/1997 Ito
5,702,347 A 12/1997 Yabe
5,707,344 A 1/1998 Nakazawa
5,725,474 A 3/1998 Yasui
5,725,476 A 3/1998 Yasui
5,725,477 A 3/1998 Yasui
5,725,478 A 3/1998 Saad
5,777,797 A 7/1998 Miyano
5,782,751 A 7/1998 Matsuno
5,810,715 A 9/1998 Moriyama
5,836,894 A 11/1998 Sarvazyan
5,860,913 A 1/1999 Yamaya
5,870,234 A 2/1999 EbbesmeierneeSchitthof
5,916,148 A 6/1999 Tsuyuki
5,940,126 A 8/1999 Kimura
6,095,970 A 8/2000 Hidaka
6,117,068 A 9/2000 Gourley
6,181,481 B1 1/2001 Yamamoto
6,196,967 B1 3/2001 Lim et al.
6,261,226 B1 7/2001 Mckenna
6,277,064 B1 8/2001 Yoon
6,359,674 B1 3/2002 Horiuchi
6,375,610 B2 4/2002 Verschuur
6,402,738 B1 6/2002 Ouchi
6,419,626 B1 7/2002 Yoon
6,476,851 B1 11/2002 Nakamura
6,638,214 B2 10/2003 Akiba
6,673,012 B2 1/2004 Fuji
6,712,760 B2 3/2004 Sano
6,832,984 B2 12/2004 Stelzer
6,888,119 B2 5/2005 Iizuka
7,435,218 B2 10/2008 Krattiger
7,621,869 B2 11/2009 Ratnakar
7,630,148 B1 12/2009 Yang
7,701,650 B2 4/2010 Lin
7,713,246 B2 5/2010 Shia
7,746,572 B2 6/2010 Asami
7,813,047 B2 10/2010 Wang
7,828,725 B2 11/2010 Maruyama
7,927,272 B2 4/2011 Bayer
7,967,745 B2 6/2011 Gliad
7,976,462 B2 7/2011 Wright
8,064,666 B2 11/2011 Bayer
8,154,663 B2 * 4/2012 Jia ...................... H04N 21/4318 348/625
8,182,422 B2 5/2012 Bayer
8,197,399 B2 6/2012 Bayer
8,235,887 B2 8/2012 Bayer
8,262,558 B2 9/2012 Sato
8,287,446 B2 10/2012 Bayer
8,289,381 B2 10/2012 Bayer
8,300,325 B2 10/2012 Katahira
8,310,530 B2 11/2012 Bayer
8,437,519 B2 5/2013 Baumgart
8,447,132 B1 5/2013 Galil
8,449,457 B2 5/2013 Aizenfeld
8,585,584 B2 11/2013 Ratnakar
8,587,645 B2 11/2013 Bayer
8,666,151 B2 * 3/2014 Kim .......................... G06T 5/92 382/162
8,672,836 B2 3/2014 Higgins
8,712,151 B2 * 4/2014 Zhao ...................... A61B 34/30 382/167
8,715,168 B2 5/2014 Ratnakar
8,797,392 B2 8/2014 Bayor
8,872,908 B2 10/2014 Bayer
8,926,502 B2 1/2015 Levy
8,933,959 B2 1/2015 Brown Elliott
9,044,185 B2 6/2015 Bayer
9,101,266 B2 8/2015 Levi
9,101,268 B2 8/2015 Levy
9,101,287 B2 8/2015 Levy
9,262,691 B2 2/2016 Kang
9,314,147 B2 4/2016 Levy
9,320,419 B2 4/2016 Kirma
9,898,686 B2 * 2/2018 Taylor .................. G06V 10/761
10,367,974 B2 * 7/2019 Kikuchi ........... A61B 1/000095
10,516,865 B2 * 12/2019 Sidar ................ A61B 1/000095
10,791,308 B2 * 9/2020 Sidar ......................... G06T 5/20
11,330,238 B2 * 5/2022 Sidar ......................... G06T 5/40
11,750,782 B2 * 9/2023 Sidar ................ A61B 1/000095 348/71
12,231,829 B2 * 2/2025 Sidar ......................... G06T 5/40
2001/0036322 A1 11/2001 Bloomfield
2002/0017515 A1 2/2002 Obata
2002/0047897 A1 4/2002 Sugimoto
2002/0087047 A1 7/2002 Remijan
2002/0105514 A1 8/2002 Roche, Jr.
2002/0109774 A1 8/2002 Meron
2002/0161281 A1 10/2002 Jaffe
2002/0172498 A1 11/2002 Esenyan
2002/0183591 A1 12/2002 Matsuura
2003/0030918 A1 2/2003 Murayama
2003/0063398 A1 4/2003 Abe
2003/0076411 A1 4/2003 Iida
2003/0083552 A1 5/2003 Remijan
2003/0099387 A1 5/2003 Doi
2003/0128893 A1 7/2003 Castorina
2003/0153897 A1 8/2003 Russo
2004/0015054 A1 1/2004 Hino
2004/0046865 A1 3/2004 Ueno
2004/0061780 A1 4/2004 Huffman
2004/0106850 A1 6/2004 Yamaya
2004/0133072 A1 7/2004 Kennedy

(56) References Cited

U.S. PATENT DOCUMENTS

| | | | |
|---|---|---|---|
| 2004/0138532 | A1 | 7/2004 | Glukhovsky |
| 2004/0158129 | A1 | 8/2004 | Okada |
| 2004/0160682 | A1 | 8/2004 | Miyano |
| 2004/0190159 | A1 | 9/2004 | Hasegawa |
| 2004/0218075 | A1 | 11/2004 | Tsuruoka |
| 2004/0249247 | A1 | 12/2004 | Iddan |
| 2005/0018042 | A1 | 1/2005 | Rovegno |
| 2005/0020876 | A1 | 1/2005 | Shioda |
| 2005/0038317 | A1 | 2/2005 | Ratnakar |
| 2005/0047134 | A1 | 3/2005 | Mueller |
| 2005/0090709 | A1 | 4/2005 | Okada |
| 2005/0096501 | A1 | 5/2005 | Stelzer |
| 2005/0117637 | A1 | 6/2005 | Routhier |
| 2005/0119527 | A1 | 6/2005 | Banik |
| 2005/0234296 | A1 | 10/2005 | Saadat |
| 2005/0234347 | A1 | 10/2005 | Yamataka |
| 2005/0251127 | A1 | 11/2005 | Brosch |
| 2005/0272975 | A1 | 12/2005 | McWeeney |
| 2005/0283048 | A1 | 12/2005 | Gil |
| 2006/0047184 | A1 | 3/2006 | Banik |
| 2006/0063976 | A1 | 3/2006 | Aizenfeld |
| 2006/0069314 | A1 | 3/2006 | Farr |
| 2006/0114986 | A1 | 6/2006 | Knapp |
| 2006/0149129 | A1 | 7/2006 | Watts |
| 2006/0171693 | A1 | 8/2006 | Todd |
| 2006/0173246 | A1 | 8/2006 | Todd |
| 2006/0183975 | A1 | 8/2006 | Saadat |
| 2006/0184037 | A1 | 8/2006 | Ince |
| 2006/0189845 | A1 | 8/2006 | Maahs |
| 2006/0215406 | A1 | 9/2006 | Thrailkill |
| 2006/0252994 | A1 | 11/2006 | Ratnakar |
| 2006/0264704 | A1 | 11/2006 | Fujimori |
| 2006/0293556 | A1 | 12/2006 | Garner |
| 2007/0015989 | A1 | 1/2007 | Desai |
| 2007/0049803 | A1 | 3/2007 | Moriyama |
| 2007/0055100 | A1 | 3/2007 | Kato |
| 2007/0079029 | A1 | 4/2007 | Carlson |
| 2007/0088193 | A1 | 4/2007 | Omori |
| 2007/0106119 | A1 | 5/2007 | Hirata |
| 2007/0142711 | A1 | 6/2007 | Bayer |
| 2007/0162095 | A1 | 7/2007 | Kimmel |
| 2007/0167681 | A1 | 7/2007 | Gili |
| 2007/0177008 | A1 | 8/2007 | Bayer |
| 2007/0177009 | A1 | 8/2007 | Bayer |
| 2007/0185384 | A1 | 8/2007 | Bayer |
| 2007/0188427 | A1 | 8/2007 | Lys |
| 2007/0197875 | A1 | 8/2007 | Osaka |
| 2007/0203396 | A1 | 8/2007 | Mccutcheon |
| 2007/0206945 | A1 | 9/2007 | Delorme |
| 2007/0213591 | A1 | 9/2007 | Aizenfeld |
| 2007/0229656 | A1 | 10/2007 | Khait |
| 2007/0244353 | A1 | 10/2007 | Larsen |
| 2007/0244354 | A1 | 10/2007 | Bayer |
| 2007/0247867 | A1 | 10/2007 | Hunter |
| 2007/0265492 | A1 | 11/2007 | Sonnenschein |
| 2007/0270642 | A1 | 11/2007 | Bayer |
| 2007/0279486 | A1 | 12/2007 | Bayer |
| 2007/0293720 | A1 | 12/2007 | Bayer |
| 2008/0021274 | A1 | 1/2008 | Bayer |
| 2008/0026413 | A1 | 1/2008 | Apostolopoulos |
| 2008/0036864 | A1 | 2/2008 | McCubbrey |
| 2008/0045797 | A1 | 2/2008 | Yasushi |
| 2008/0058593 | A1 | 3/2008 | Gu et al. |
| 2008/0058601 | A1 | 3/2008 | Fujimori |
| 2008/0071290 | A1 | 3/2008 | Larkin |
| 2008/0130108 | A1 | 6/2008 | Bayer |
| 2008/0151070 | A1 | 6/2008 | Shiozawa |
| 2008/0161646 | A1 | 7/2008 | Gomez |
| 2008/0163652 | A1 | 7/2008 | Shatskin |
| 2008/0167529 | A1 | 7/2008 | Otawara |
| 2008/0177139 | A1 | 7/2008 | Courtney |
| 2008/0183034 | A1 | 7/2008 | Henkin |
| 2008/0183043 | A1 | 7/2008 | Spinnler |
| 2008/0221388 | A1 | 9/2008 | Seibel et al. |
| 2008/0226148 | A1 | 9/2008 | Gu |
| 2008/0253686 | A1 | 10/2008 | Bayer |
| 2008/0262312 | A1 | 10/2008 | Carroll |
| 2008/0275298 | A1 | 11/2008 | Ratnakar |
| 2008/0303898 | A1 | 12/2008 | Nishimura |
| 2009/0005643 | A1 | 1/2009 | Smith |
| 2009/0023998 | A1 | 1/2009 | Ratnakar |
| 2009/0030275 | A1 | 1/2009 | Nicolaou |
| 2009/0054790 | A1 | 2/2009 | Czaniera |
| 2009/0062615 | A1 | 3/2009 | Yamaya |
| 2009/0086017 | A1 | 4/2009 | Miyano |
| 2009/0135245 | A1 | 5/2009 | Luo |
| 2009/0137875 | A1 | 5/2009 | Kitagawa |
| 2009/0143647 | A1 | 6/2009 | Banju |
| 2009/0147076 | A1 | 6/2009 | Ertas |
| 2009/0149706 | A1 | 6/2009 | Yamazaki |
| 2009/0182917 | A1 | 7/2009 | Kim |
| 2009/0213211 | A1 | 8/2009 | Bayer |
| 2009/0216084 | A1 | 8/2009 | Yamane |
| 2009/0231419 | A1 | 9/2009 | Bayer |
| 2009/0234183 | A1 | 9/2009 | Abe |
| 2009/0253966 | A1 | 10/2009 | Ichimura |
| 2009/0287188 | A1 | 11/2009 | Golden |
| 2009/0287192 | A1 | 11/2009 | Vivenzio |
| 2009/0299144 | A1 | 12/2009 | Shigemori |
| 2010/0010309 | A1 | 1/2010 | Kitagawa |
| 2010/0016673 | A1 | 1/2010 | Bandy |
| 2010/0053312 | A1 | 3/2010 | Watanabe |
| 2010/0069713 | A1 | 3/2010 | Endo |
| 2010/0073470 | A1 | 3/2010 | Takasaki |
| 2010/0073948 | A1 | 3/2010 | Stein |
| 2010/0076268 | A1 | 3/2010 | Takasugi |
| 2010/0123950 | A1 | 5/2010 | Fujiwara |
| 2010/0130822 | A1 | 5/2010 | Katayama |
| 2010/0141763 | A1 | 6/2010 | Itoh |
| 2010/0160729 | A1 | 6/2010 | Smith |
| 2010/0174144 | A1 | 7/2010 | Hsu |
| 2010/0231702 | A1 | 9/2010 | Tsujimura |
| 2010/0245653 | A1 | 9/2010 | Bodor |
| 2010/0249513 | A1 | 9/2010 | Tydlaska |
| 2010/0280322 | A1 | 11/2010 | Mizuyoshi |
| 2010/0296178 | A1 | 11/2010 | Genet |
| 2011/0034769 | A1 | 2/2011 | Adair |
| 2011/0063427 | A1 | 3/2011 | Fengler |
| 2011/0140003 | A1 | 6/2011 | Beck |
| 2011/0160530 | A1 | 6/2011 | Ratnakar |
| 2011/0160535 | A1 | 6/2011 | Bayer |
| 2011/0164127 | A1 | 7/2011 | Stehle |
| 2011/0169931 | A1 | 7/2011 | Pascal |
| 2011/0184243 | A1 | 7/2011 | Wright |
| 2011/0211267 | A1 | 9/2011 | Takato |
| 2011/0263938 | A1 | 10/2011 | Levy |
| 2011/0282144 | A1 | 11/2011 | Gettman |
| 2011/0292258 | A1 | 12/2011 | Adler |
| 2012/0040305 | A1 | 2/2012 | Karazivan |
| 2012/0050606 | A1 | 3/2012 | Debevec |
| 2012/0053407 | A1 | 3/2012 | Levy |
| 2012/0057251 | A1 | 3/2012 | Takato |
| 2012/0065468 | A1 | 3/2012 | Levy |
| 2012/0076425 | A1 | 3/2012 | Brandt |
| 2012/0209071 | A1 | 8/2012 | Bayer |
| 2012/0209287 | A1 | 8/2012 | Zhao |
| 2012/0209289 | A1 | 8/2012 | Duque |
| 2012/0212630 | A1 | 8/2012 | Pryor |
| 2012/0220832 | A1 | 8/2012 | Nakade |
| 2012/0224026 | A1 | 9/2012 | Bayer |
| 2012/0229615 | A1 | 9/2012 | Kirma |
| 2012/0232340 | A1 | 9/2012 | Levy |
| 2012/0232343 | A1 | 9/2012 | Levy |
| 2012/0242665 | A1 | 9/2012 | Peng |
| 2012/0253121 | A1 | 10/2012 | Kitano |
| 2012/0277535 | A1 | 11/2012 | Hoshino |
| 2012/0300999 | A1 | 11/2012 | Bayer |
| 2013/0053646 | A1 | 2/2013 | Yamamoto |
| 2013/0057724 | A1 | 3/2013 | Miyahara |
| 2013/0066297 | A1 | 3/2013 | Shtul |
| 2013/0085329 | A1 | 4/2013 | Morrissette |
| 2013/0109916 | A1 | 5/2013 | Levy |
| 2013/0116506 | A1 | 5/2013 | Bayer |
| 2013/0131447 | A1 | 5/2013 | Benning |

(56) References Cited

U.S. PATENT DOCUMENTS

| | | | |
|---|---|---|---|
| 2013/0137930 | A1 | 5/2013 | Menabde |
| 2013/0150671 | A1 | 6/2013 | Levy |
| 2013/0162768 | A1 | 6/2013 | Lie |
| 2013/0163666 | A1 | 6/2013 | Leontaris |
| 2013/0169843 | A1 | 7/2013 | Ono |
| 2013/0172670 | A1 | 7/2013 | Levy |
| 2013/0172676 | A1 | 7/2013 | Levy |
| 2013/0197309 | A1 | 8/2013 | Sakata |
| 2013/0197556 | A1 | 8/2013 | Shelton |
| 2013/0222640 | A1 | 8/2013 | Baek |
| 2013/0264465 | A1 | 10/2013 | Dai |
| 2013/0267778 | A1 | 10/2013 | Rehe |
| 2013/0271588 | A1 | 10/2013 | Kirma |
| 2013/0274551 | A1 | 10/2013 | Kirma |
| 2013/0281925 | A1 | 10/2013 | Benscoter |
| 2013/0296649 | A1 | 11/2013 | Kirma |
| 2013/0303979 | A1 | 11/2013 | Stieglitz |
| 2013/0314559 | A1 | 11/2013 | Kim |
| 2013/0317295 | A1 | 11/2013 | Morse |
| 2014/0018624 | A1 | 1/2014 | Bayer |
| 2014/0031627 | A1 | 1/2014 | Jacobs |
| 2014/0046136 | A1 | 2/2014 | Bayer |
| 2014/0107418 | A1 | 4/2014 | Ratnakar |
| 2014/0148644 | A1 | 5/2014 | Levi |
| 2014/0213850 | A1 | 7/2014 | Levy |
| 2014/0225998 | A1 | 8/2014 | Dai |
| 2014/0253580 | A1 | 9/2014 | Kubo |
| 2014/0276207 | A1 | 9/2014 | Ouyang |
| 2014/0296628 | A1 | 10/2014 | Kirma |
| 2014/0296643 | A1 | 10/2014 | Levy |
| 2014/0296866 | A1 | 10/2014 | Salman |
| 2014/0309495 | A1 | 10/2014 | Kirma |
| 2014/0316198 | A1 | 10/2014 | Krivopisk |
| 2014/0316204 | A1 | 10/2014 | Ofir |
| 2014/0320617 | A1 | 10/2014 | Parks |
| 2014/0333742 | A1 | 11/2014 | Salman |
| 2014/0333743 | A1 | 11/2014 | Gilreath |
| 2014/0336459 | A1 | 11/2014 | Bayer |
| 2014/0343358 | A1 | 11/2014 | Hameed |
| 2014/0343361 | A1 | 11/2014 | Salman |
| 2014/0343489 | A1 | 11/2014 | Lang |
| 2014/0364691 | A1 | 12/2014 | Krivopisk |
| 2014/0364692 | A1 | 12/2014 | Salman |
| 2014/0364694 | A1 | 12/2014 | Avron |
| 2015/0005581 | A1 | 1/2015 | Salman |
| 2015/0042775 | A1 | 2/2015 | Zhao |
| 2015/0045614 | A1 | 2/2015 | Krivopisk |
| 2015/0049177 | A1 | 2/2015 | Johansson |
| 2015/0057500 | A1 | 2/2015 | Salman |
| 2015/0094536 | A1 | 4/2015 | Wieth |
| 2015/0099925 | A1 | 4/2015 | Davidson |
| 2015/0099926 | A1 | 4/2015 | Davidson |
| 2015/0105618 | A1 | 4/2015 | Levy |
| 2015/0164308 | A1 | 6/2015 | Ratnakar |
| 2015/0182105 | A1 | 7/2015 | Salman |
| 2015/0196190 | A1 | 7/2015 | Levy |
| 2015/0201827 | A1 | 7/2015 | Sidar |
| 2015/0208900 | A1 | 7/2015 | Vidas |
| 2015/0208908 | A1 | 7/2015 | Davidson |
| 2015/0223676 | A1 | 8/2015 | Bayer |
| 2015/0230698 | A1 | 8/2015 | Cline |
| 2015/0235613 | A1 | 8/2015 | Yamada |
| 2015/0305601 | A1 | 10/2015 | Levi |
| 2015/0313445 | A1 | 11/2015 | Davidson |
| 2015/0313450 | A1 | 11/2015 | Wieth |
| 2015/0313451 | A1 | 11/2015 | Salman |
| 2015/0320300 | A1 | 11/2015 | Gershov |
| 2015/0342446 | A1 | 12/2015 | Levy |
| 2015/0358415 | A1 | 12/2015 | Lang |
| 2015/0374206 | A1 | 12/2015 | Shimony |
| 2016/0015257 | A1 | 1/2016 | Levy |
| 2016/0015258 | A1 | 1/2016 | Levin |
| 2016/0058268 | A1 | 3/2016 | Salman |
| 2016/0335751 | A1 | 11/2016 | Sidar |
| 2017/0084026 | A1 | 3/2017 | Kim |

FOREIGN PATENT DOCUMENTS

| | | |
|---|---|---|
| CA | 2812097 | 3/2012 |
| CA | 2798716 | 6/2013 |
| CA | 2798729 | 6/2013 |
| CN | 103348470 | 10/2013 |
| CN | 103403605 | 11/2013 |
| CN | 103491854 | 1/2014 |
| CN | 103702604 | 4/2014 |
| CN | 103732120 | 4/2014 |
| CN | 105246393 | 1/2016 |
| CN | 105324065 | 2/2016 |
| CN | 105324066 | 2/2016 |
| CN | 105338875 | 2/2016 |
| CN | 105358042 | 2/2016 |
| CN | 105358043 | 2/2016 |
| CN | 105377106 | 3/2016 |
| CN | 105407788 | 3/2016 |
| CN | 104717916 | 6/2016 |
| DE | 202010016900 | 6/2011 |
| EP | 1690497 | 8/2006 |
| EP | 1835844 | 9/2007 |
| EP | 1968425 | 9/2008 |
| EP | 1986541 | 11/2008 |
| EP | 1988813 | 11/2008 |
| EP | 2023794 | 2/2009 |
| EP | 2023795 | 2/2009 |
| EP | 2190341 | 6/2010 |
| EP | 2211683 | 8/2010 |
| EP | 2457492 | 5/2012 |
| EP | 2457493 | 5/2012 |
| EP | 1988812 | 11/2012 |
| EP | 2520218 | 11/2012 |
| EP | 2604175 | 6/2013 |
| EP | 2618718 | 7/2013 |
| EP | 2635932 | 9/2013 |
| EP | 2648602 | 10/2013 |
| EP | 2649648 | 10/2013 |
| EP | 2672878 | 12/2013 |
| EP | 2736400 | 6/2014 |
| EP | 2744390 | 6/2014 |
| EP | 2 749 201 A1 | 7/2014 |
| EP | 2442706 | 11/2014 |
| EP | 2908714 | 8/2015 |
| EP | 2979123 | 2/2016 |
| EP | 2991537 | 3/2016 |
| EP | 2994032 | 3/2016 |
| EP | 2994033 | 3/2016 |
| EP | 2994034 | 3/2016 |
| EP | 2996536 | 3/2016 |
| EP | 2996541 | 3/2016 |
| EP | 2996542 | 3/2016 |
| EP | 2996621 | 3/2016 |
| EP | 2865322 | 4/2016 |
| GB | 12196628 | 3/2016 |
| JP | H1043129 | 2/1998 |
| JP | H10239740 | 9/1998 |
| JP | 11137512 | 6/1999 |
| JP | 2005253543 | 9/2005 |
| JP | 2006025888 | 2/2006 |
| JP | 2006068109 | 3/2006 |
| JP | 2010178766 A | 8/2010 |
| JP | 2012135432 | 7/2012 |
| JP | 2013116277 A2 | 6/2013 |
| JP | 2013123647 | 6/2013 |
| JP | 2013123648 | 6/2013 |
| JP | 2013208459 | 10/2013 |
| JP | 2013215582 | 10/2013 |
| JP | 2013230383 | 11/2013 |
| JP | 2013542467 | 11/2013 |
| JP | 2013544617 | 12/2013 |
| JP | 2014524303 | 9/2014 |
| JP | 2014524819 | 9/2014 |
| JP | 2015533300 | 11/2016 |
| WO | 2006073676 | 7/2006 |
| WO | 2006073725 | 7/2006 |
| WO | 2007070644 | 6/2007 |

(56) References Cited

FOREIGN PATENT DOCUMENTS

| | | | |
|---|---|---|---|
| WO | 2007092633 | | 8/2007 |
| WO | 2007092636 | | 8/2007 |
| WO | 2007087421 | | 11/2007 |
| WO | 2007136859 | | 11/2007 |
| WO | 2007136879 | | 11/2007 |
| WO | 2008015164 | | 2/2008 |
| WO | 2009014895 | | 1/2009 |
| WO | 2009015396 | | 1/2009 |
| WO | 2009049322 | | 4/2009 |
| WO | 2009049324 | | 4/2009 |
| WO | 2009062179 | | 5/2009 |
| WO | 2010146587 | | 12/2010 |
| WO | 2012038958 | | 3/2012 |
| WO | 2012056453 | | 5/2012 |
| WO | 2012075153 | A2 | 6/2012 |
| WO | 2012077116 | | 6/2012 |
| WO | 2012077117 | | 6/2012 |
| WO | 2012096102 | | 7/2012 |
| WO | 2012120507 | | 9/2012 |
| WO | 2013014673 | | 1/2013 |
| WO | 2013024476 | | 2/2013 |
| WO | 2014061023 | | 4/2014 |
| WO | 2014160983 | | 10/2014 |
| WO | 2014179236 | | 11/2014 |
| WO | 2014182723 | | 11/2014 |
| WO | 2014182728 | | 11/2014 |
| WO | 2014183012 | | 11/2014 |
| WO | 2014186230 | | 11/2014 |
| WO | 2014186519 | | 11/2014 |
| WO | 2014186521 | | 11/2014 |
| WO | 2014186525 | | 11/2014 |
| WO | 2014186775 | | 11/2014 |
| WO | 2014210516 | | 12/2014 |
| WO | 2015002847 | | 1/2015 |
| WO | 2015047631 | | 4/2015 |
| WO | 2015050829 | | 4/2015 |
| WO | 2015084442 | | 6/2015 |
| WO | 2015095481 | | 6/2015 |
| WO | 2015112747 | | 7/2015 |
| WO | 2015112899 | | 7/2015 |
| WO | 2015134060 | | 9/2015 |
| WO | 2015168066 | | 11/2015 |
| WO | 2015168664 | | 11/2015 |
| WO | 2015171732 | | 11/2015 |
| WO | 2015175246 | | 11/2015 |
| WO | 2016014581 | | 1/2016 |
| WO | 2016033403 | | 3/2018 |

OTHER PUBLICATIONS

Evaluation of contrast limited adaptive histogram equalization CLAHE on a FPGA; 2008; (Year: 2008).*

Ferguson et al., "Evaluation of Contrast Limited Adaptive Histogram Equalization (CLAHE) Enhancement on a FPGA" 2008 IEEE International SOC Conference. pp. 119-122.

Office Action date Feb. 26, 2016 for U.S. Appl. No. 14/274,323.

Office Action dated Feb. 4, 2016 for U.S. Appl. No. 14/271,234.

International Search Report for PCT/US14/37004, Sep. 25, 2014.

International Search Report for PCT/US2014/037526, Oct. 16, 2014.

International Search Report for POT/US14/38094, Nov. 6, 2014.

International Search Report for PCT/US2015/012751, mailed on Jun. 26, 2015.

International Search Report for PCT/US2014/58143, mailed on Jan. 21, 2015.

International Search Report for PCT/US2014/071085, mailed on Mar. 27. 2015.

International Search Report for PCT/US2015/027902, mailed on Jul. 23. 2016.

International Search Report for PCT/US2015/012506, mailed on Dec. 11, 2015.

International Search Report for PCT/US2015/29421, malled on Aug. 7, 2015.

International Search Report for PCT/US2015/28962, mailed on Jul. 28, 2015.

International Search Report for PCT/US2016/47334, mailed on Dec. 28, 2015.

International Search Report for PCT/US2015/41396, mailed on Sep. 29, 2015.

International Search Report for PCT/US2015/66486, mailed on Dec. 17, 2015.

International Search Report for PCT/US2015/6548, mailed on Feb. 26, 2016.

Corrected Notice of Allowance dated Apr. 13, 2016 for U.S. Appl. No. 13/680,646.

Notice of Allowance dated Mar. 28. 2016 for U.S. Appl. No. 13/413,059.

Notice of Allowance dated Mar. 29, 2016 for U.S. Appl. No. 13/680,646.

Office Action dated Mar. 23, 2016 for U.S. Appl. No. 13/713,449.

Office Action dated Mar. 24, 2016 for U.S. Appl. No. 13/212,627.

Office Action dated Mar. 28, 2016 for U.S. Appl. No. 13/119,032.

Office Action dated May 25, 2016 for U.S. Appl. No. 14/271,234.

Office Action dated May 5, 2016 for U.S. Appl. No. 14/278,338.

Office Action dated May 5, 2016 for U.S. Appl. No. 14/263,896.

Image color conversion; 2010 (Year: 201 0).

Evaluation of contrast limited adaptive histogram equalization; enhancement on FPGA; 2008. (Year: 2008).

* cited by examiner

ENDOSCOPIC IMAGE ENHANCEMENT USING CONTRAST LIMITED ADAPTIVE HISTOGRAM EQUALIZATION (CLAHE) IMPLEMENTED IN A PROCESSOR

CROSS-REFERENCE TO RELATED APPLICATIONS

This application is a continuation of U.S. Nonprovisional patent application Ser. No. 18/353,271, filed on Jul. 17, 2023, which is a continuation of U.S. Nonprovisional patent application Ser. No. 17/658,689, filed on Apr. 11, 2022, now U.S. Pat. No. 11,750,782, issued on Sep. 5, 2023, which is a continuation of U.S. Nonprovisional patent application Ser. No. 16/992,312, filed on Aug. 13, 2020, now U.S. Pat. No. 11,330,238, issued on May 10, 2022, which is a continuation of U.S. Nonprovisional patent application Ser. No. 16/685,299, filed on Nov. 15, 2019, now U.S. Pat. No. 10,791,308, issued on Sep. 29, 2020, which is a continuation of U.S. Nonprovisional patent application Ser. No. 15/155,814, filed on May 16, 2016, now U.S. Pat. No. 10,516,865, issued on Dec. 24, 2019, which claims the benefit of U.S. Provisional Patent Application No. 62/162,788, filed on May 17, 2015, and U.S. Provisional Patent Application No. 62/259,683, filed on Nov. 25, 2015. Each of the above-mentioned applications is herein incorporated by reference in its entirety.

FIELD

The present specification relates generally to endoscopy systems and more particularly, to a multiple viewing elements endoscopy system that enhances imaging by implementing a contrast limited adaptive histogram equalization (CLAHE) algorithm in a processor, preferably a field programmable gate array (FPGA).

BACKGROUND

Endoscopes have attained great acceptance within the medical community since they provide a means for performing procedures with minimal patient trauma while enabling the physician to view the internal anatomy of the patient. Over the years, numerous endoscopes have been developed and categorized according to specific applications, such as cystoscopy, colonoscopy, laparoscopy, and upper GI endoscopy and others. Endoscopes may be inserted into the body's natural orifices or through an incision in the skin.

An endoscope is usually an elongated tubular shaft, rigid or flexible, having a video camera or a fiber optic lens assembly at its distal end. The shaft is connected to a handle which sometimes includes an ocular for direct viewing. Viewing is also usually possible via an external screen. Various surgical tools may be inserted through a working channel in the endoscope for performing different surgical procedures.

Endoscopes, such as colonoscopes, that are currently being used typically have a front camera for viewing the internal organ, such as the colon, an illuminator, a fluid injector for cleaning the camera lens and sometimes also the illuminator, and a working channel for insertion of surgical tools, for example, for removing polyps found in the colon. Often, endoscopes also have fluid injectors ("jet") for cleaning a body cavity, such as the colon, into which they are inserted. The illuminators commonly used are fiber optics which transmit light, generated remotely, to the endoscope tip section. The use of light-emitting diodes (LEDs) for illumination is also known.

Current endoscopes provide limited options to control image characteristics of video images displayed by them. Contrast Limited Adaptive Histogram Equalization (CLAHE) is an image processing algorithm that is used for intensifying the contrast of both luminance and color in image regions depending upon a user defined processing threshold. As a result of the intensification, fine details are enhanced, and thus, may be better detected and diagnosed by a physician.

There is a need in the art for image processing methods that may be implemented within the size and hardware limitations of medical devices, such as endoscopes, and which also provide an option to control contrast and/or noise in color and video images and thereby enhance the images.

SUMMARY

The following embodiments and aspects thereof are described and illustrated in conjunction with systems, tools and methods, which are meant to be exemplary and illustrative, not limiting in scope. The present application discloses numerous embodiments.

In some embodiments, the present specification discloses a controller for a multiple viewing elements endoscope system, comprising: a base board module; a field programmable gate array (FPGA) configured to implement a contrast limited adaptive histogram equalization (CLAHE) algorithm to enhance images obtained by said multiple viewing elements system.

Optionally, said FPGA comprises an adapter having conversion modules. Still optionally, said FPGA comprises a frame grabber. Optionally, said FPGA comprises a fetching module. Still optionally, said FPGA comprises an interpolation algorithm. Still optionally, said FPGA further comprises a histogram controller.

Optionally, said base board module further comprises DDR3 memory in communication with said frame grabber.

In some embodiments, the present specification discloses a method of enhancing images obtained by a multiple viewing elements endoscope system using a contrast limited adaptive histogram equalization (CLAHE) algorithm wherein said endoscope system includes a controller having a baseboard module comprising a processor, such as a general processing unit or field programmable gate array (FPGA), configured to implement said algorithm, said method comprising the steps of: inputting YCbCr color space video streams to an adapter on said processor; converting said YCbCr color space video streams to Lab color space video streams within said adapter; pushing said Lab color space video streams to a frame grabber on said processor; grabbing said Lab color space video streams as Lab color space frames within said frame grabber; pulling said Lab color space frames from the frame grabber using a fetching module on said processor; rearranging Lab color space frame data within said fetching module to generate delayed Lab streams; pushing said delayed Lab streams to separate modules within an interpolation algorithm on said processor; and processing said delayed Lab streams with said CLAHE algorithm within said separate modules to generate contrast enhanced Lab streams.

Optionally, converting said YCbCr color space streams to Lab color space video streams comprises the steps of: performing YCbCr to RGB conversion using MAD instantiation; performing a function similar to Y(x)=x^2.40 using a LUT; performing RGB to XYZ conversion using MAD instantiation; executing a function similar to Y(x)=x^0.33 using a LUT; and performing XYZ to Lab conversion using MAD instantiation.

Optionally, said method further comprises converting said contrast enhanced Lab streams to contrast enhanced YCbCr streams. Still optionally, said converting the contrast enhanced Lab streams to contrast enhanced YCbCr streams comprises the steps of: performing Lab to XYZ conversion using MAD instantiation; executing a function similar to Y(x)=x^0.33 using a LUT; performing XYZ to RGB conversion using MAD instantiation; performing a function similar to Y(x)=x^(1/2.40) using a LUT; and performing RGB to YCbCr conversion using MAD instantiation.

In some embodiments, the present specification discloses a method of enhancing images obtained by at least two viewing elements in an endoscope system using a contrast limited adaptive histogram equalization (CLAHE) process wherein said endoscope system includes a controller having a baseboard module comprising a field programmable gate array (FPGA) configured to implement said process, said method comprising the steps of: inputting two YCbCr color space video streams from at the least two viewing elements to an adapter on said FPGA, each viewing element providing one YCbCr color space video stream; converting the at least two YCbCr color space video streams to corresponding at least two Lab color space video streams within said adapter; pushing the at least two Lab color space video streams to a frame grabber on said FPGA; grabbing the at least two Lab color space video streams as corresponding at least two Lab color space frames within said frame grabber; pulling the at least two Lab color space frames from the frame grabber using a fetching module on said FPGA; rearranging Lab color space frame data within said fetching module to generate at least two delayed Lab streams corresponding to the at least two Lab color space frames pulled by the fetching module; pushing the at least two delayed Lab streams to corresponding at least two separate modules within an interpolation algorithm on said FPGA; and processing each delayed Lab stream with said CLAHE algorithm within said separate modules to generate at least two contrast enhanced Lab streams.

Optionally, converting a YCbCr color space stream to a Lab color space video stream comprises the steps of: performing YCbCr to RGB conversion using MAD instantiation; performing a function similar to Y(x)=x^2.40 using a LUT; performing RGB to XYZ conversion using MAD instantiation; executing a function similar to Y(x)=x^0.33 using a LUT; and performing XYZ to Lab conversion using MAD instantiation.

Optionally, the method of enhancing images obtained by at least two viewing elements further comprises converting each of the at least two contrast enhanced Lab streams to corresponding at least two contrast enhanced YCbCr streams.

Optionally, converting each contrast enhanced Lab stream to a contrast enhanced YCbCr stream comprises the steps of: performing Lab to XYZ conversion using MAD instantiation; executing a function similar to Y(x)=x^0.33 using a LUT; performing XYZ to RGB conversion using MAD instantiation; performing a function similar to Y(x)=x^(1/2.40) using a LUT; and performing RGB to YCbCr conversion using MAD instantiation.

Optionally the method of enhancing images wherein the images are obtained from three viewing elements comprises the steps of: inputting three YCbCr color space video streams from the three viewing elements to an adapter on said FPGA; converting the three YCbCr color space video streams to corresponding three Lab color space video streams within said adapter; pushing the three Lab color space video streams to a frame grabber on said FPGA in form of a video stream obtained from a single viewing element, a Y input of the frame grabber being fed by a first viewing element's Lab color space video stream, a Cb input of the frame grabber being fed by a second viewing element's Lab color space video stream, and a Cr input of the frame grabber being fed by a third viewing element's Lab color space video stream; grabbing the three Lab color space video streams as corresponding three Lab color space frames within said frame grabber; pulling the three Lab color space frames from the frame grabber using a fetching module on said FPGA; rearranging Lab color space frame data of the three Lab color space frames within said fetching module to generate three delayed Lab streams corresponding to the three Lab color space frames pulled by the fetching module; pushing the three delayed Lab streams to corresponding three separate modules within an interpolation algorithm on said FPGA; and processing each delayed Lab stream with said CLAHE algorithm within said separate modules to generate three contrast enhanced Lab streams being a first, a second and a third contrast enhanced Lab stream, each contrast enhanced Lab stream corresponding to a viewing element of the endoscope.

Optionally, the first viewing element is a left viewing element of the endoscope, the second viewing element is a central viewing element of the endoscope, and the third viewing element is a right viewing element of the endoscope.

Optionally, the first of the three contrast enhanced Lab streams is displayed as a first image on one or more display screens coupled with the controller, the second of the three contrast enhanced Lab streams is displayed as a second image on one or more display screens coupled with the controller, and the third of the three contrast enhanced Lab streams is displayed as a third image on one or more display screens coupled with the controller.

Optionally, each contrast enhanced Lab stream is displayed as a contrast enhanced image on a display device coupled with the controller, each contrast enhanced image comprising a plurality of frames having a higher degree of contrast as compared to the corresponding plurality of frames in the corresponding image obtained from a viewing element of the endoscope before being processed using the image enhancement method of the present specification.

The aforementioned and other embodiments of the present specification shall be described in greater depth in the drawings and detailed description provided below.

BRIEF DESCRIPTION OF THE DRAWINGS

These and other features and advantages of the present invention will be appreciated, as they become better understood by reference to the following detailed description when considered in connection with the accompanying drawings, wherein.

DETAILED DESCRIPTION

Figure 1:
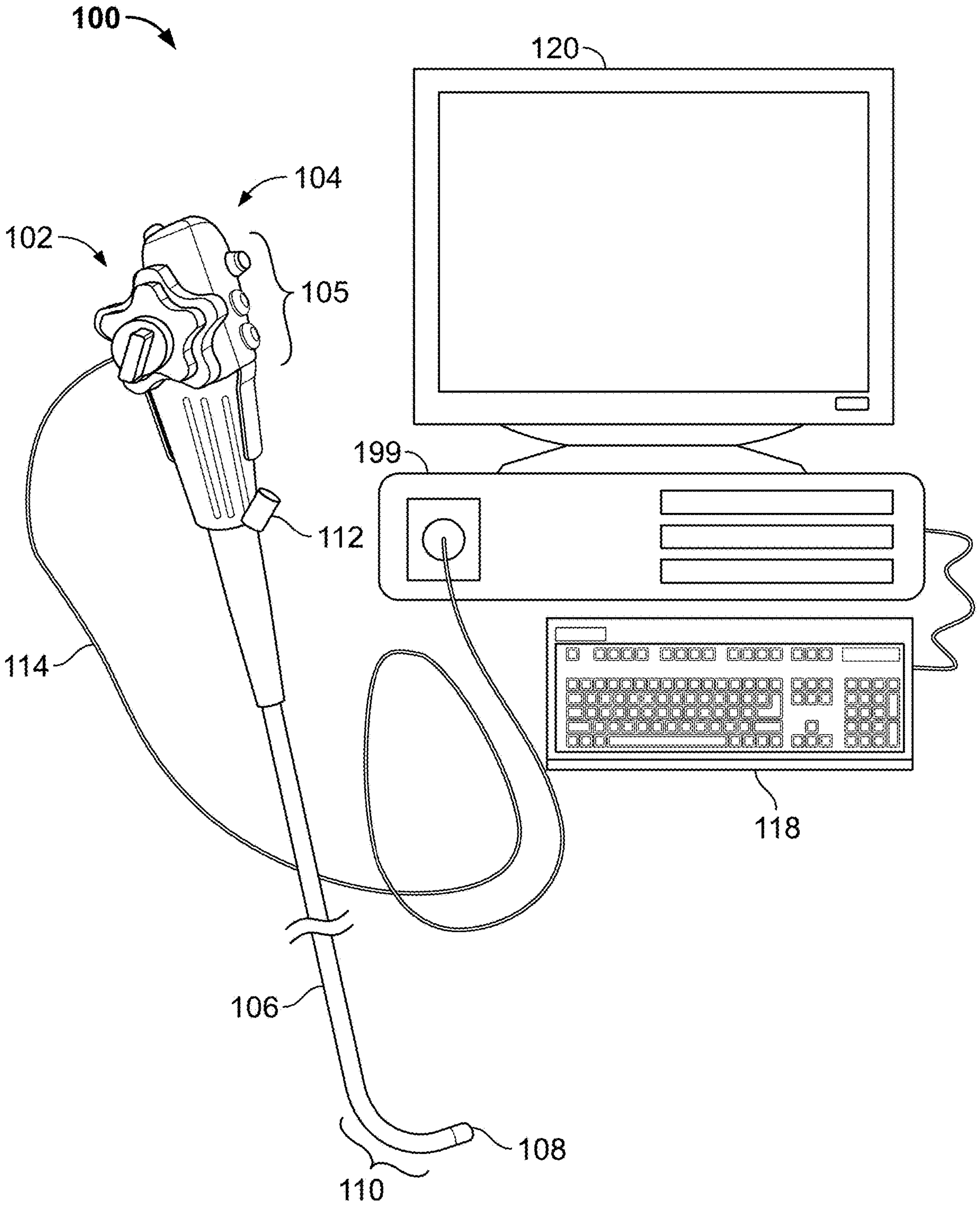
FIG. 1 illustrates a multiple camera endoscopy system, according to some embodiments of the present specification.

The present specification discloses systems and methods for enhancing images by using a contrast limited adaptive histogram equalization (CLAHE) algorithm in a processor, such as a field programmable gate array (FPGA). The images may be obtained by the imaging elements of a multiple imaging elements endoscope of an endoscopy system.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention. In the description and claims of the application, each of the words "comprise" "include" and "have", and forms thereof, are not necessarily limited to members in a list with which the words may be associated.

As used herein, the indefinite articles "a" and "an" mean "at least one" or "one or more" unless the context clearly dictates otherwise.

It should be noted herein that any feature or component described in association with a specific embodiment may be used and implemented with any other embodiment unless clearly indicated otherwise.

Embodiments of methods and/or devices of the specification may involve performing or completing selected tasks manually, automatically, or a combination thereof. Some embodiments of the specification are implemented with the use of components that comprise hardware, software, firmware or combinations thereof. In some embodiments, some components are general-purpose components such as general purpose computers or oscilloscopes. In some embodiments, some components are dedicated or custom components such as circuits, integrated circuits or software.

For example, in some embodiments, at least a portion of the methods may be implemented as a plurality of software instructions executed by a data processor, which may be part of a general-purpose or custom computer. In some embodiments, the data processor or computer comprises volatile memory for storing instructions and/or data and/or a non-volatile storage, for example, a magnetic hard-disk and/or removable media, for storing instructions and/or data. In some embodiments, implementation includes a network connection. In some embodiments, implementation includes a user interface, generally comprising one or more input devices (e.g., allowing input of commands and/or parameters) and output devices (e.g., allowing reporting parameters of operation and results).

It is appreciated that certain features of the specification, which are, for clarity, described in the context of separate embodiments, may also be provided in combination in a single embodiment. Conversely, various features of the specification, which are, for brevity, described in the context of a single embodiment, may also be provided separately or in any suitable sub-combination or as suitable in any other described embodiment of the specification. Certain features described in the context of various embodiments are not to be considered essential features of those embodiments, unless the embodiment is inoperative without those elements.

It is noted that the term "endoscope" as mentioned to herein may refer particularly to a colonoscope, according to some embodiments, but is not limited only to colonoscopes. The term "endoscope" may refer to any instrument used to examine the interior of a hollow organ or cavity of the body.

It should also be noted that a plurality of terms, as follows, appearing in this specification are used interchangeably to apply or refer to similar components and should in no way be construed as limiting:

"Utility tube/cable" may also be referred to as an "umbilical tube/cable"

A "main control unit" may also be referred to as a "controller unit", "main controller" or "fuse box".

A "viewing element" may also be referred to as an image capturing device/component, viewing components, camera, TV camera or video camera.

A "working channel" may also be referred to as a "service channel".

An "illuminator" may also be referred to as an "illumination source", and in some embodiments, an LED.

A "flexible shaft" may also be referred to as a bending section or vertebra mechanism.

A "video stream" refers to a series of individual frames.

It should be appreciated that, when the methods and systems of the present embodiment are applied to a video stream, they are applied to each individual frame, on a frame-by-frame, or group of frames, basis.

Further, as used in this specification, the term "camera" is used to describe a device for capturing light. Thus, a camera, in some embodiments, comprises at least one optical lens assembly. In some embodiments, the term "camera' is used to describe an optical lens assembly and its associated image sensor. In some embodiments, the term "camera" is used to describe an optical imaging system, such as a lens assembly or assemblies and associated solid state detector arrays. In some embodiments, the terms "viewing element" and "camera" may be used interchangeably.

As used in the specification, the term "optical assembly" is used to describe a set of components that allows the endoscopic device to capture light and transform that light into at least one image. In some embodiments, lenses/optical elements are employed to capture light and image capturing devices, such as sensors, are employed to transform that light into at least one image.

Image capturing devices may be Charged Coupled Devices (CCD's) or Complementary Metal Oxide Semiconductor (CMOS) image sensors, or other suitable devices having a light sensitive surface usable for capturing an image. In some embodiments, a sensor such as a Charge Coupled Device (CCD) or a Complementary Metal Oxide Semiconductor (CMOS) image sensor (for detecting the reflected light received by an optical element), is employed.

In some embodiments, an optical element comprises a plurality of optics such as lens assemblies, lenses and protective glass, and is configured to receive reflected light from target objects.

An optical assembly, as used in the specification, comprises at least one lens assembly, its associated sensor(s), and its associated circuit board. In some embodiments, an "optical assembly" may comprise more than one viewing element or camera, associated sensor(s), and associated circuit board(s). In some embodiments, an "optical assembly" may comprise a front viewing element, its associated sensor, and its associated circuit board. In some embodiments, an "optical assembly" may comprise a front viewing element, its associated sensors, and its associated circuit board and/or at least one side viewing element, its associated sensors and its associated circuit boards. Further, the optical assembly typically is associated with at least one illuminator for illuminating the field of view. Thus, for example, a front-pointing optical assembly includes a front-pointing viewing element with associated sensor, associated circuit board and is associated with at least one illuminator.

Endoscopes that are currently being used typically have a front and side viewing elements for viewing the internal organs, illuminators, a fluid injector for cleaning the lens of the viewing elements, and sometimes also illuminators and a working channel for insertion of surgical tools. The illuminators commonly used are fiber optics that transmit light, generated remotely, to the endoscope tip section. The use of light-emitting diodes (LEDs) for illumination is also known.

A tip section of the endoscope assembly may be inserted into a patient's body through a natural body orifice, such as the mouth, nose, urethra, vagina, or anus.

In accordance with an embodiment of the present specification, a tip cover may house the tip section. The tip section, with the tip cover, may be turned or maneuvered by way of a flexible shaft, which may also be referred to as a bending section, for example, a vertebra mechanism. Tip cover may be configured to fit over the inner parts of the tip section, including an electronic circuit board assembly and a fluid channeling component, and to provide protection to the internal components in the inner parts, such as a body cavity. The endoscope can then perform diagnostic or surgical procedures inside the body cavity. The tip section carries one or more viewing elements, such as cameras, to view areas inside body cavities that are the target of these procedures.

Tip cover may include panels having a transparent surface, window or opening for optical lens assemblies of viewing elements. The panels and viewing elements may be located at the front and sides of the tip section. Optical lens assemblies may include a plurality of lenses, static or movable, providing different fields of view.

An electronic circuit board assembly may be configured to carry the viewing elements, which may view through openings on the panels. Viewing elements may include an image sensor, such as but not limited to a Charge Coupled Device (CCD) or a Complementary Metal Oxide Semiconductor (CMOS) image sensor.

The electronic circuit board assembly may be configured to carry illuminators that are able to provide illumination through illuminator optical windows. The illuminators may be associated with viewing elements, and may be positioned to illuminate the viewing elements' fields of view.

One or more illuminators may illuminate the viewing fields of the viewing elements. In an embodiment, the illuminators may be fiber optic illuminators that carry light from remote sources. The optical fibers are light carriers that carry light from a remotely located light source to the illuminators. The optical fibers extend along an insertion tube between the tip section at a distal end of the endoscope, and a handle at a proximal end. An umbilical/utility tube connects the handle to a main control unit. The main control unit enables control of several functions of the endoscope assembly, including power delivered and communication of signals between the endoscope and its display, among others.

Reference is now made to FIG. 1, which shows a multi-viewing elements endoscopy system 100. System 100 may include a multi-viewing elements endoscope 102. Multi-viewing elements endoscope 102 may include a handle 104, from which an elongated shaft 106 emerges. Elongated shaft 106 terminates with a tip section 108 which is turnable by way of a bending section 110. Handle 104 may be used for maneuvering elongated shaft 106 within a body cavity. The handle may include one or more buttons and/or knobs and/or switches 105 which control bending section 110 as well as functions such as fluid injection and suction. Handle 104 may further include at least one, and in some embodiments, one or more working channel openings 112 through which surgical tools may be inserted as well as one and more side service channel openings.

A utility cable 114, also referred to as an umbilical tube, may connect between handle 104 and a Main Control Unit 199. Utility cable 114 may include therein one or more fluid channels and one or more electrical channels. The electrical channel(s) may include at least one data cable for receiving video signals from the front and side-pointing viewing elements, as well as at least one power cable for providing electrical power to the viewing elements and to the discrete illuminators.

The main control unit 199 contains the controls required for displaying the images of internal organs captured by the endoscope 102. The main control unit 199 may govern power transmission to the endoscope's 102 tip section 108, such as for the tip section's viewing elements and illuminators. The main control unit 199 may further control one or more fluid, liquid and/or suction pump(s) which supply corresponding functionalities to the endoscope 102. One or more input devices 118, such as a keyboard, a touch screen and the like may be connected to the main control unit 199 for the purpose of human interaction with the main control unit 199. In the embodiment shown in FIG. 1, the main control unit 199 comprises a screen/display 120 for displaying operation information concerning an endoscopy procedure when the endoscope 102 is in use. The screen 120 may be configured to display images and/or video streams received from the viewing elements of the multi-viewing element endoscope 102. The screen 120 may further be operative to display a user interface for allowing a human operator to set various features of the endoscopy system.

Optionally, the video streams received from the different viewing elements of the multi-viewing element endoscope 102 may be displayed separately on at least one monitor (not seen) by uploading information from the main control unit 199, either side-by-side or interchangeably (namely, the operator may switch between views from the different viewing elements manually). Alternatively, these video streams may be processed by the main control unit 199 to combine them into a single, panoramic video frame, based on an overlap between fields of view of the viewing elements. In an embodiment, two or more displays may be connected to the main control unit 199, each for displaying a video stream from a different viewing element of the multi-viewing element endoscope 102. The main control unit 199 is described in U.S. patent application Ser. No. 14/263,896, entitled "Video Processing in a Compact Multi-Viewing Element Endoscope System" and filed on Apr. 28, 2014, which is herein incorporated by reference in its entirety.

Figure 2:
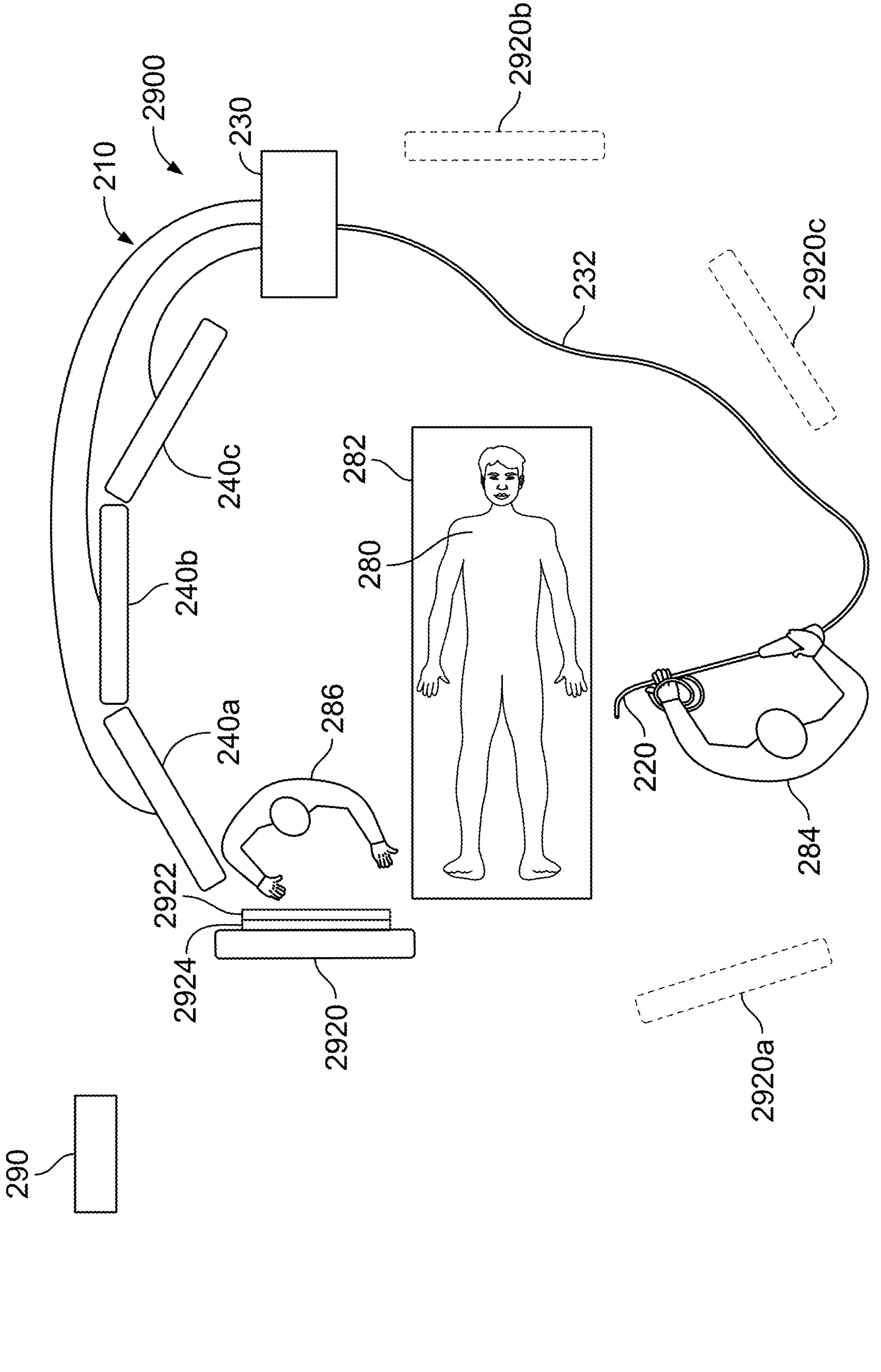
FIG. 2 schematically depicts an exemplary layout of an endoscopy system and an interface unit deployed in an operating room, according to an embodiment of the present specification.

FIG. 2 schematically depicts a layout of an endoscope system 210 and an associated interface unit 2900 deployed in an operating room, according to some embodiments. A patient 280 is supported on a bed 282 and a physician 284 may employ an endoscope 220 of endoscope system 210 in an endoscopic procedure. An assistant 286 assists physician 284 on the other side of bed 282 across from physician 284.

Endoscope 220 is connected to a main controller 230 by a utility cable 232. In embodiments, endoscope 220 provides three simultaneous endoscopic views using three cameras housed in the tip of endoscope 220. Main controller 230 is connected to three display screens, 240*a*, 240*b*, and 240*c*, wherein each display screen may be configured to display a corresponding view of the three endoscopic views provided by endoscope system 210, substantially as described above. Display screens 240*a*, 240*b*, and 240*c* are positioned facing physician 284 and possibly elevated so that physician 284 may conduct the endoscopic procedure by looking at the screen displays and having an undisturbed line of site thereto. In some embodiments, display screens 240*a*, 240*b*, and 240*c* are in the form of a single large screen.

Interface unit 2900 comprises an image processor encased with main controller 230, and an interface unit display 2920 functionally associated with the image processor. The image processor simultaneously receives image data associated with the three views provided by endoscope 220 from three respective imaging channels and generates images comprising image data from the three views, wherein the images are displayable on interface unit display 2920. For example, the three cameras of endoscope 220 may provide three incoming video streams, respectively, and the image processor may then generate a single video stream comprising image data from the three incoming video streams, substantially as described above.

According to some embodiments, interface unit display 2920 is functionally associated with the image processor encased with main controller 230 by a cable. In some embodiments, interface unit display 2920 is wirelessly associated with the image processor. According to some embodiments, interface unit display 2920 is substantially portable and may be deployed in a multitude of positions within the operating room. Moreover, according to some embodiments, interface unit display 2920 may be easily displaced from position to position within the operating room during a procedure. For example, interface unit display 2920*b* or 2920*c* may be positioned so that both physician 284 and assistant 286 can watch the screen thereof, or interface unit display 2920*a* may be positioned facing assistant 286.

In some embodiments, interface unit 2900 comprises an interface unit computer, functionally associated with main controller 230 and with the image processor encased therewith.

In some embodiments, interface unit 2900 comprises a user interface module 2922 associated with interface unit display 2920, and assistant 286 may employ user interface module 2922 to command interface unit 2900 and/or interface unit computer, and/or endoscope system 210. For example, assistant 286 may employ user interface module 2922 to input and store, in the interface unit computer, patient-related textual information, such as relevant biographical data, before or during an endoscopic procedure. According to some embodiments, user interface module 2922 comprises a touch screen 2924.

According to some embodiments, interface unit computer may communicate with a computer network, substantially as described above and using an access point 290 installed in the operating room and allowing access to such a computer network. Access point 290 may comprise a LAN connector to which the interface unit computer is connected through a LAN cable. According to some embodiments, access point 290 may be a Wi-Fi modem with which the interface unit computer may communicate wirelessly.

Figure 3:
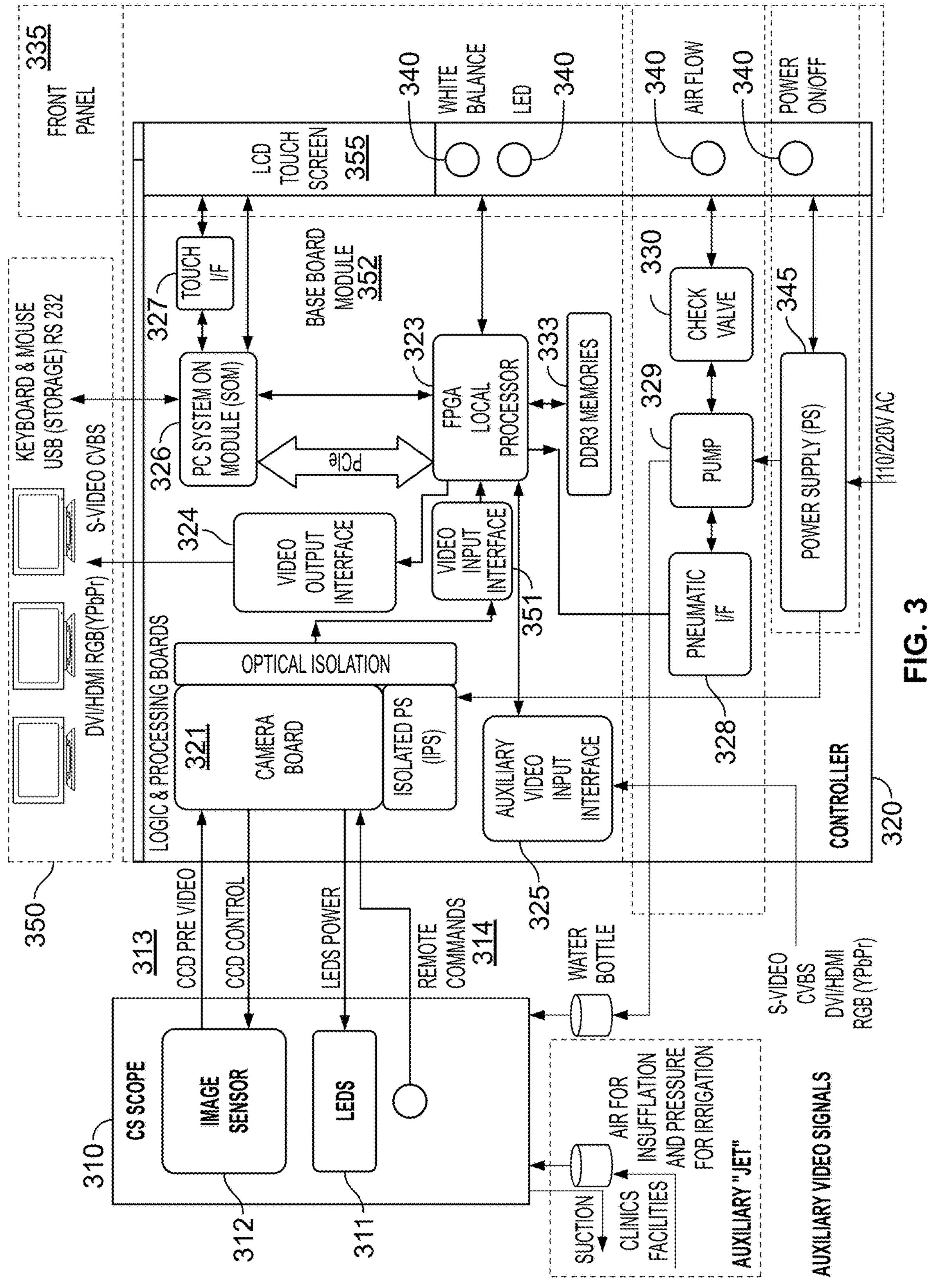
FIG. 3 is a block diagram illustrating an exemplary video processing architecture, according to an embodiment of the present specification.

FIG. 3 is a circuit/component diagram detailing the operative connection between a video controller or a controller circuit board 320 of the main control unit 199 of FIG. 1 and endoscope 310 and display units 350. Referring to FIG. 3, video controller/controller circuit board 320 comprises a camera board 321 that controls the power supplies to LEDs 311, transmits controls for the operation of image sensor(s) 312 (corresponding to one or more cameras) in the endoscope, and converts pre-video signals 313 from image sensors 312 to standard video signals. Image sensor(s) 312 may be charge coupled devices (CCD) or complementary metal oxide semiconductor (CMOS) imagers. Camera board 321 receives pre-video signal(s) 313 generated by the CCD imagers and also other remote commands 314 from the endoscope 310.

The controller circuit board 320 further comprises elements for processing video obtained from image sensors 312 through camera board 321, as well as other elements for system monitoring and control. All these elements are connected with a Base Board Module 352, which is a printed circuit board (PCB). In various embodiments, some of these elements are integrated circuits (ICs) that are connected by soldering, an element 326 (SOM or System on Module) is connected by mounting, while all other elements are connected by means of cables.

Various elements connected with the Base Board Module 352 are described as follows:

FPGA (Field Programmable Gate Array) 323:

An FPGA 323 is a programmable logic device that may be customized for the system requirements and performs tasks that may be categorized by two types: logic tasks which are preferably implemented by hardware (as opposed to software), and logic tasks related to video image processing. In one embodiment, Base Board Module 352 may include one or more double data rate type three synchronous dynamic random access memory modules (DDR3) 333 in communication with FPGA 323.

Logic tasks that are preferably implemented by hardware may include, but are not limited to:

1. Initializing some Base Board Module's 352 ICs upon system power-up;
2. Monitoring buttons 340 for White Balance, LED on/off, Air Flow, and Power on/off on front-panel 335;
3. Monitoring SOM's 326 proper operation using a watch-dog mechanism;
4. Backing-up some of the system's parameters (example: airflow level), even while the system is switched off; and
5. Communicating with Camera Board 321.

Logic tasks related to video image processing (that may have software-configurable parameters) include, and may not be limited to:

1. Multiplexing video inputs—Each of the multiple imaging elements has several video interfaces that are multiplexed via a Video Input Interface 351. Further, in some embodiments, several auxiliaries are multiplexed via an Auxiliary Video Input Interface 325.
2. Internal test pattern to video outputs via Video Output Interface 324 to multiple displays.
3. Conversion between cameras' video standard to display video standard.
4. OSD (On Screen Display) insertion, also known as graphic overlay.
5. PIP (Picture-in-Picture).
6. Stitching images from several cameras into one image displayed on a single screen.
7. Image adjustments, such as brightness, contrast, etc.

Auxiliary Video Input Interface 325:

In one optional embodiment, the video input to Auxiliary Video Input Interface 325 may comprise analog video, such as in color, video, blanking, sync (CVBS), S-Video or $YP_BP_R$ format or digital video (DVI), and may be displayed as such.

SOM (System on Module) 326:

The SOM 326 may provide an interface to input devices such as keyboard, mouse, and touchscreen via Touch I/F 327. Through these input devices, together with buttons 340 in Front Panel 335, the user may control the system's functionality and operational parameters. In one embodiment, a peripheral component interconnect express (PCIe) bus connects SOM 326 with FPGA 323. Types of data traffic over the PCIe may include:

a. SOM 326 to FPGA 323: Commands (for example, when the user changes operational parameters); and
b. FPGA 323 to SOM 326: Registers values, which provide an indication of the internal status, and captured images.

Other Functionalities:

Controller circuit board 320 may further control one or more fluid, liquid and/or suction pump(s) which supply corresponding functionalities to the endoscope through a pneumatic I/F 328, a pump 329 and a check valve 330. Controller circuit board 320 may further comprise an on-board power supply 345 and a front panel 335 that may provide operational buttons 340 for the user.

Camera board 321 may receive video signal(s) 313 which, in one embodiment, comprises three video feeds, corresponding to video pickups by three endoscopic tip viewing elements (one front and two side-looking viewing elements), as generated by the corresponding image sensor(s) 312. In one embodiment, the three video feed pickups, corresponding to the three viewing elements (the front-looking, left-side looking and right-side looking viewing elements) of an endoscopic tip, are displayed on three respective monitors.

As discussed above, FPGA 323 includes logic modules for various purposes, in accordance with embodiments of the specification. In some embodiments, FPGA 323 implements a contrast limited adaptive histogram equalization (CLAHE) algorithm in order to enhance imaging. CLAHE is an image processing algorithm to intensify the contrast of both luminance and color in image regions where differences between neighboring pixels are small. As a result, fine details are enhanced that may be better detected and diagnosed by a physician. In embodiments, an endoscope using CLAHE may provide enhanced images of polyps or blood vessels on an intestine wall. In embodiments, these images are real-time video images captured by one or more cameras of the endoscope.

Figure 4A:
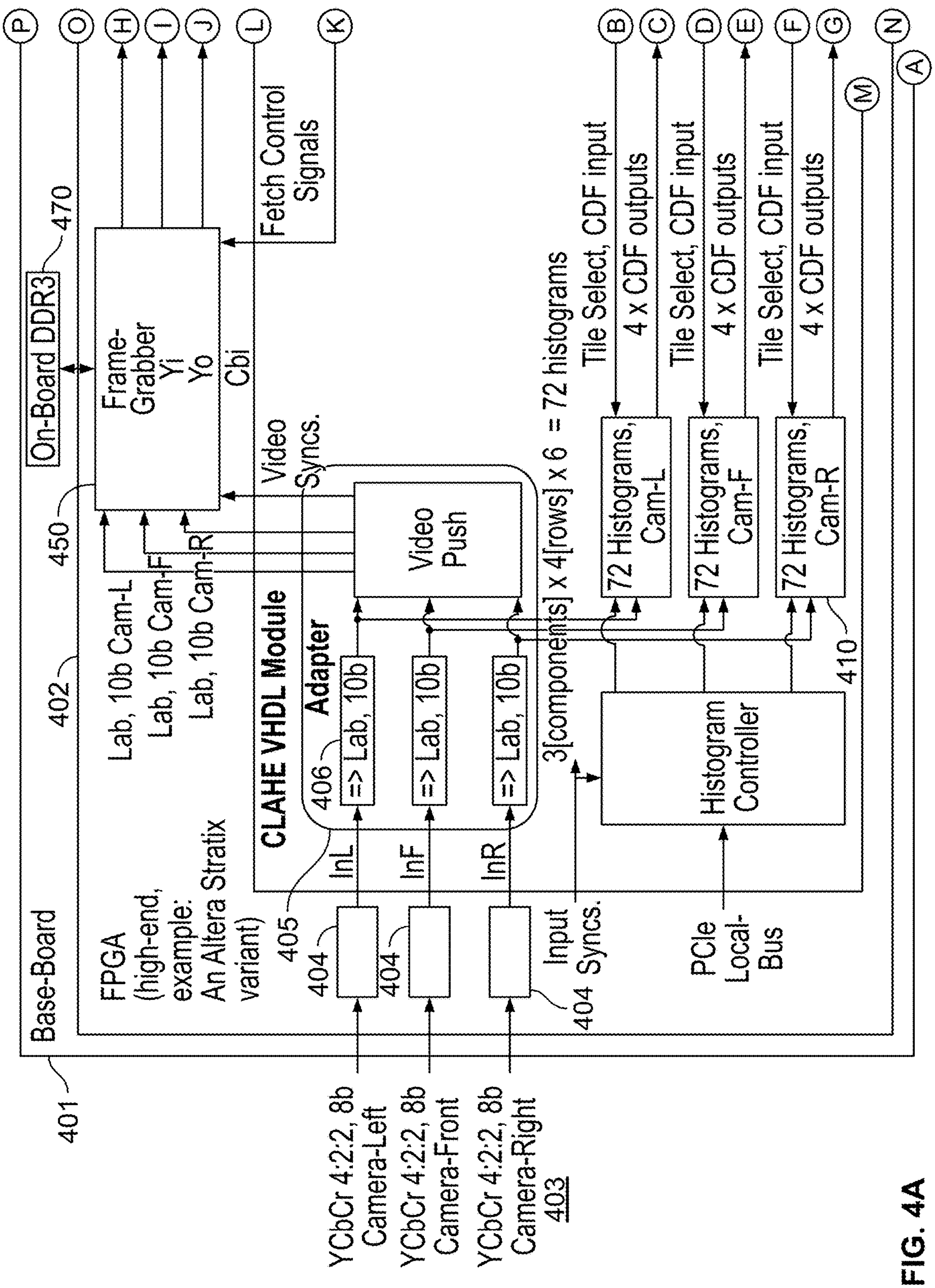
FIG. 4A illustrates components of a field programmable gate array (FPGA) and its periphery, according to an embodiment of the present specification.
Figure 4A:
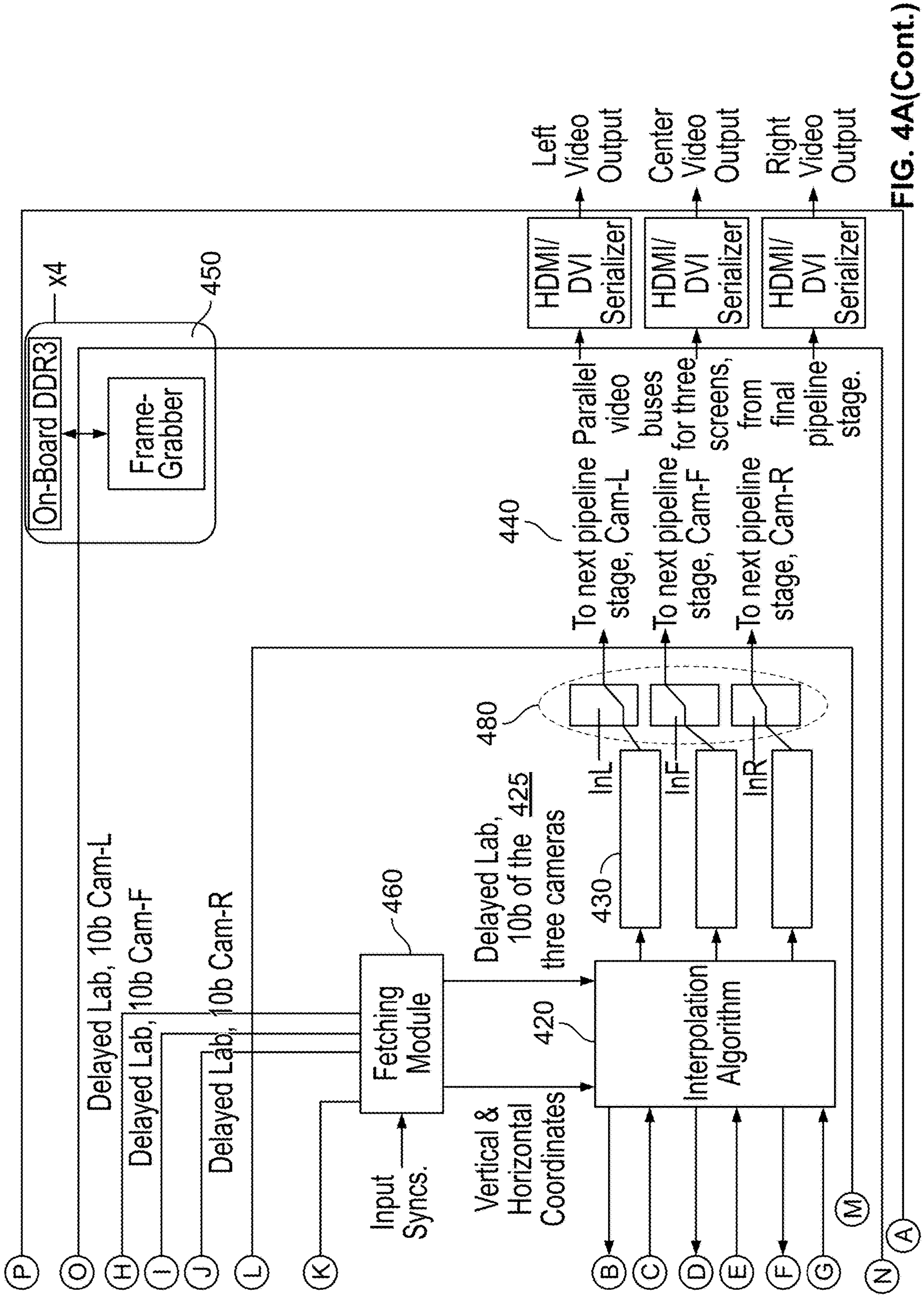

FIG. 4A illustrates components of an FPGA 402, which may be similar to FPGA 323 of FIG. 3, in accordance with some embodiments of the present specification. FIG. 4A also illustrates a DDR3 memory device 470 in communication with FPGA 402. In some embodiments, FPGA 402 and DDR3 memory device 470 are located in a base board module 401 within an endoscope system. In embodiments, FPGA 402 receives images captured by all viewing elements in the endoscope system. In alternative embodiments, each viewing element may be in communication with a FPGA, similar to FPGA 402.

In some embodiments, YCbCr input 403 from each viewing element is input through pipelines 404 to an adapter 405. In some embodiments, each YCbCr input is 8 bit, 10 bit, or of any other length per component. In one embodiment, the YCbCr input for adapter 405 are of 10 bit per component. The adapter 405 includes "Lab, 10*b*" modules 406. The adapter 405 converts YCbCr input 403 used as a part of the color image pipeline to a Lab color space, in accordance with some embodiments. A "Lab" color space is a color space with dimension 'L' for lightness and 'a' and 'b' for the color-opponent dimensions, based on nonlinearly compressed coordinates. The Lab color space includes all perceivable colors. Lab color space is designed to be perceptually uniform, and allows correlation of image contrast enhancement of an algorithm used herein and described subsequently, with its perceptual quality. A bitmap image represented as Lab requires more data per pixel to obtain the same precision as its counterpart YCbCr bitmap. In some embodiments, each YCbCr input 403 including 10 bit per color component is converted by the adapter 405 to a 12 bit per component Lab color space video stream, of which all 12 bits are used for the L component, whereas 10 bits are used for each of a and b color components, totaling 32 bits per Lab pixel.

The video stream, i.e. set of frames, generated by the adapter 405 may be driven to two different destinations, and thus may have at least two purposes. The first purpose is, in some embodiments, to drive a delay line comprising on-board DDR3 470 and an FPGA-internal frame grabber 450. In some embodiments, one frame delay (if video is progressive, when interlaced, as is the case with current NTSC sensors where the delay is one video field) may be introduced through the delay line. In alternative embodiments, the delay line may be implemented as an FPGA-internal memory. As mentioned above, DDR3 470 delay line path, fed from adapter 405, uses 12 bits for L component and 10 bits for each of a and b components (32 bit in total for one Lab pixel). In some embodiments, DDR3 470 supports eight banks per memory, of which two banks are used for the frame delay line.

In some embodiments, the FPGA 402 comprises a single FPGA-internal frame grabber 450, common to all viewing elements. It should be appreciated that the FPGA 402, in some embodiments, comprises a plurality of FPGA-internal frame grabbers, similar to the frame grabber 450. In some embodiments, there are at least three FPGA-internal frame grabbers, one corresponding to each of the three viewing elements or cameras of the endoscope. Also, each of the plurality of frame grabbers has an onboard DDR3 memory (similar to the DDR3 470). Thus, base board 401 includes a plurality of DDR3 memory components associated with the plurality of frame grabbers. In still further embodiments, use of the on-board DDR3 memory, for the delay line, is optional in order to reduce latency and spare hardware.

In embodiments, frame grabber 450 is fed with three video streams (one per viewing element), each comprising a Lab color space. Individual frames from the streams are converted by adapter 405 to form compatible digital video streams. One of the functions implemented by adapter 405 is to make the video stream feeding the frame grabber 450 appear as if it is input from a single viewing element, and not multiple viewing elements (such as the three viewing elements used for the purpose of this description). In some embodiments, frame grabber's 450 Y input is fed by a left viewing element's Lab, Cb input by a central viewing element's Lab, and Cr input by a right viewing element's Lab, meaning that frame grabber 450 is fed by three viewing elements. This mode of operation may be advantageous in using a single frame grabber (for use with one camera endoscopes in accordance with some embodiments) with a multiple camera endoscope.

In some embodiments, Lab color space frames, corresponding to the three viewing elements, are fetched from the frame grabber 450 by a fetching module 460. The fetching module 460 may keep track of the ingress video frame timing (for example, line count). In embodiments, fetching module 460 may instruct frame grabber 450 on which rows to fetch from DDR3 470. These rows are calculated from the video lines that may be needed to be displayed, and which are at constant phase shift relative to the ingress frame. Fetching module 460 also rearranges the data from fetched rows to a format understood by an interpolation algorithm 420. The data from the fetched rows may include three video streams (one per each viewing element) where each video stream comprises Lab components. The delayed Lab streams, corresponding to each viewing element, are fed to separate modules within interpolation algorithm 420 where they are similarly processed in accordance with the CLAHE algorithm of the present specification.

As discussed, the video stream generated by the adapter 405 may be driven to two different destinations, and thus may have at least two purposes. For the second purpose, a second path output from the adapter 405 uses 6 bit per each Lab component to send to elements 410 that build and store histogram information in accordance with various embodiments of the present specification. The image information output from adapter 405 may be perceived to be split into several tiles by elements 410. Units of the tile heights are in video lines and the tile widths are in pixels. Tiles may be described by attributes, such as key vertical coordinates including start, center, and end. In embodiments, each tile overlaps with its neighboring tiles. Overlapping may reduce the tiling or bordering effect. As understood by those skilled in the art, a result of the tiling effect is that an image may appear to contain vertical and/or horizontal line(s) going through the tile centers. The vertical/horizontal lines may appear to divide the image into distinct rectangular regions, corresponding to the tiles. The rectangular regions may differ in their luminance and/or chrominance.

In embodiments, overlapping tiles to the maximum (50% theoretical—approximately 48% in practice—on each side, per axis) may mitigate the tiling effect to a reasonable extent. In addition, using bi-cubic instead of bi-linear interpolation for inter-tile interpolation, may further reduce the tiling effect. It should be appreciated, that the higher the percentage overlap, the better is the reduction or mitigation of the tiling effect. At the same time, reducing the percentage overlap may increase the level of local enhancement of the image since the tiles can become smaller. Independently, both the locality of enhancement of the image and tiling effect improve as number of tiles increases. In some embodiments, 64 tiles are used/arranged as an 8×8 array, that is, an 8 vertical×8 horizontal tile structure.

Latency is necessary in any real-time CLAHE implementation, regardless of the type of platform running the algorithm. Practical latency is between 30% to 100% frame—meaning it is unnoticeable to the human eye (under normal circumstances of 24 frames per seconds or higher), provided the accumulative latency due to other elements in the system does not reach a critical limit. The CLAHE latency is caused due to the fact that before the interpolation algorithm 420 can fetch CDF (Cumulative Distribution Function) values from a pair (pair, due to the bilinear interpolation in some embodiments) of histogram (tile) rows, sufficient time must be allowed for all the pixels covered by said two rows of tiles to flow into the FPGA 402 and build the relevant histograms. With the more preferable bi-cubic inter-tile interpolation, in various embodiments, yet longer latency is required as instead of two rows, four rows need be fetched. Also, the step of transforming a histogram to a CDF by clipping, integration and normalization (as well as other processes) adds more latency. For example, if there are four histogram (tiles) rows, and a pair of rows is needed for interpolation, the order of magnitude of latency will approach 50% frame. A preferred practical latency would be 100% frame (if video is progressive) or 100% field (if video is interlaced)—this is because gamut fitting (i.e. minimization of out-of-gamut problem) requires first grabbing an entire frame (or field) to extract its ingress (I) and enhanced (E) statistics (min, average., max) as part of building the CDF functions. It should be noted that a 100% delay also covers the case of fetching of four tile rows as is required by the bi-cubic interpolation.

Per ingress video line, specific actions are performed by the CLAHE algorithm. For example, at a row 0, video lines covered by the tiles of row 0 are 0-70. Therefore, sometime before the start of these lines (line 238, for example, the end of previous frame), the histograms are reset. In lines 0-70, the histograms are being built, therefore immediately afterwards, to reduce latency, lines 71-75 (76-79 are safety margins or spare) convert the histograms to CDFs. To support the case where row 0 participates in a bilinear interpolation (together with a row 1), only after row 1 finishes its own CDF generation (at ingress line 135), can the first video line participating in the row 0+1 interpolation be fetched and transmitted to the screen (line 36—center of row 0). This example also demonstrates the CLAHE latency: when line 36 is transmitted to the screen (or next pipeline stage), the ingress video line is already 136, hence latency is (136−36)/240=42% of a frame (in actual, an NTSC field). However, this example applies only in the embodiments where bi-linear inter-tile interpolation is used, and, gamut fitting is not required.

Three histograms may be allocated for each tile, such that each histogram corresponds to a color component (L/a/b). The histograms may form distribution functions of the Lab values related with the ingress pixels that are covered by the tile. FIG. 4A illustrates a group of memory elements incorporated into elements 410 that correspond to one viewing element. Elements 410 may describe 384 histograms (1[viewing element]×3[color components of lab]×8[rows of histograms]×8[histograms per row]×2[buffers]). The two buffers are needed in the case of 100% delay which necessitates that one buffer of histograms collect the ingress video and get built, while the other buffer hold the histograms of the previous frame and is converted to an array of CDFs. In the next ingress video frame, the buffers swap roles. This technique is called double-buffering. In another embodiment where double-buffering is not implemented, elements 410 may describe 72 histograms (3 components×4 rows×6 tiles=72). Similarly, in yet another embodiment, elements 410 may describe 192 histograms (3 components×8 rows×8 tiles=192).

In some embodiments, each histogram is based on one FPGA-internal 9K-bit memory module providing 512 bins of 18 bit each. In alternative embodiments, the numbers of histograms may vary, for example the number could be 8×8 histograms per color component. In alternative embodiments, to reach high FPGA utilization efficiency, number of bins per histograms (and, CDF) may be reduced from 512 to, for example, 64 with said one 9K-bit memory module supporting 8 histograms instead of 1. In the embodiments of 64bin CDF representation, the FPGA uses bi-linear interpolation between two adjacent CDF bins, to improve accuracy to a level comparable with that of higher order CDFs (256 bins, 512 bins etc.).

In embodiments, a threshold may be set by a user, for the histogram bins. In embodiments, the threshold is given by the user through a SOM-run GUI aided with an input interface (keyboard, mouse, touchscreen). In embodiments, upon physician's disconnecting the endoscope and system folding back to displaying a pattern generator, the user-defined thresholds are automatically bypassed by the FPGA 402 to be 0, so the pattern generator's appearance will seem natural to the user (threshold of 0 is equivalent to CLAHE deactivation). Once an endoscope is connected again, the bypass is cancelled; hence original user-defined thresholds are restored. An alternate means of bypassing comprises usage of the original Lab pixels at the output of the delay lines as the output of the CLAHE, without replacing them with the CDF values—hence the CDFs are bypassed altogether. The bins may be clipped beyond the set threshold level. Additionally, excess samples after clipping may be equally distributed over all the histogram's bins. As a result, the user may be able to control contrast and/or noise of an image that is subsequently displayed.

It should be appreciated that the user-defined thresholds are preferably determined by a user based upon what he or she considers to be a pleasant contrast. The theoretical threshold range is [0,1], where zero means no enhancement at all, or deactivation of the CLAHE process, and one means maximum enhancement, which is the maximum color enhancement of CLAHE that is equal to the maximum of CDF bins difference in the tile plus the interpolation. The maximum value can be normalized to other ranges as well according to the bit depth of the image and the tile size.

Figure 4B:
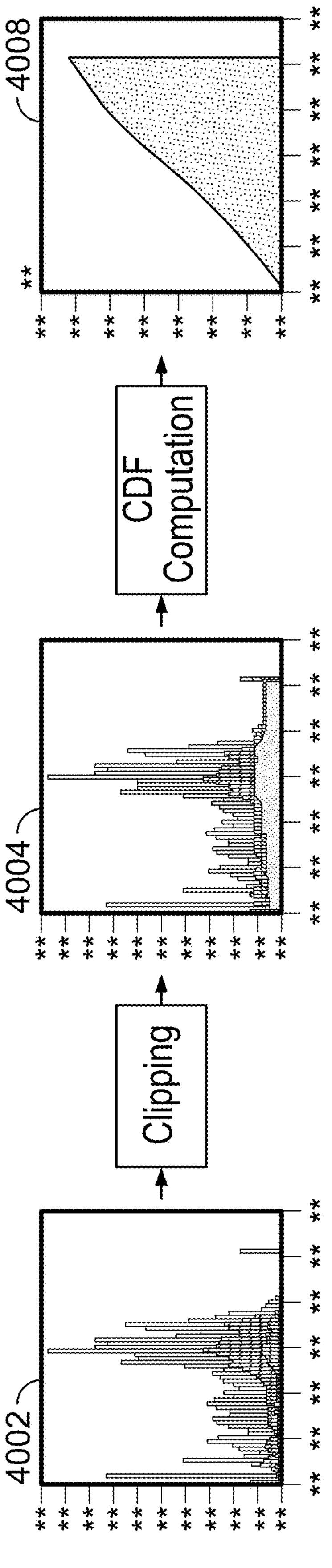
FIG. 4B illustrates derivation of a cumulative distribution function (CDF) achieved by clipping a histogram using a low threshold, according to an embodiment of the present specification.
Figure 4C:
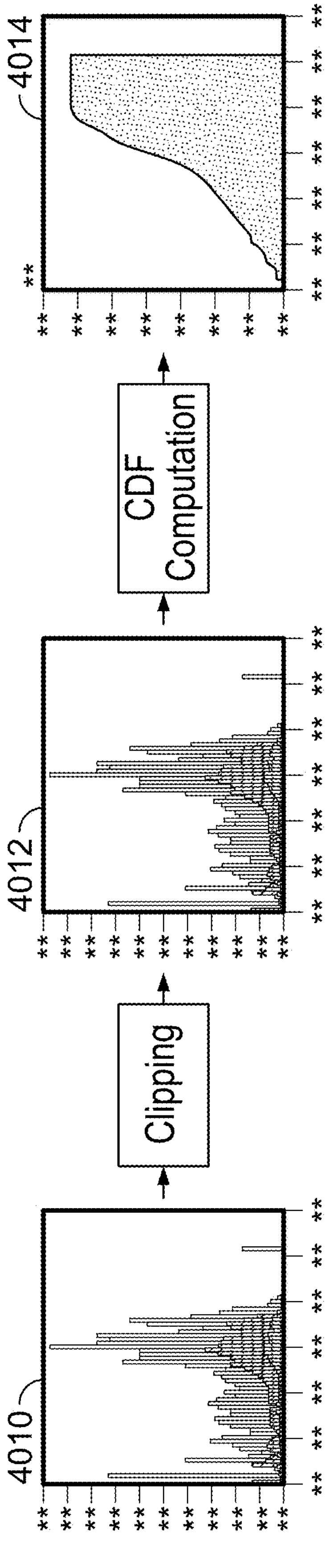
FIG. 4C illustrates derivation of a CDF achieved by clipping a histogram, using a higher threshold than shown in FIG. 4B, according to an embodiment of the present specification.

FIG. 4B illustrates derivation of a CDF by clipping a histogram, using a low threshold, in accordance with an embodiment of the present specification. As shown histogram 4002 is clipped to firstly obtain an intermediary chart 4004 which upon computation results in CDF 4008. Due to application of a lower threshold during clipping, the resulting CDF 4008 resembles an identity function (straight line, constant slope). FIG. 4C illustrates derivation of a CDF by clipping a histogram, using a higher threshold, in accordance with an embodiment of the present specification. As shown histogram 4010 is clipped to firstly obtain an intermediary chart 4012 which upon computation results in CDF 4014. Due to the application of a higher threshold during clipping, the resulting CDF 4014 has a steep slope in the region where the histogram peaks, whereas in other regions, the slope is moderate. In embodiments, a clipping threshold level is determined empirically, and may be based on a physician's preference. For a given measure of contrast enhancement, clipping threshold may be lowered as number of histograms (per color component) increase. This is caused because increasing number of histograms for the same resolution results in fewer pixels covered by a histogram. Inversely, clipping threshold may be increased as image resolution increases for the same number of tiles. This is caused because there are now more pixels covered by a histogram. It should be noted that in some embodiments, the clipping threshold can be set per a specific color component (L/a/b) of a specific camera (left, front, right) of the endoscopes. This is useful, for example, in cases where side cameras (left and right side viewing cameras) may have different CLAHE requirements from the front camera, or where the luminance (L) may have different CLAHE requirements from the color (a, b).

The modified histograms, with optionally controlled contrast and noise, may be converted into Cumulative Distribution Functions (CDFs) and normalized, so that CDF bin content corresponding to a highest bin number may represent full-scale value of an L, a, or b component. The resulting normalized CDFs may be used as Look-Up Tables (LUTs) whose input may be the L, a, and b pixel values. Output of the LUTs may be corresponding L, a, and b pixel values of modified contrast.

Referring back to FIG. 4A, output of elements 410 and 10 bit delayed Lab stream 425 may simultaneously be fed to interpolation algorithm module 420. Stream 425 provides information related to the original Lab values of the ingress pixels to interpolation algorithm module 420. The information is provided on a per-pixel basis. Module 420 may utilize the Lab values as input corresponding to relevant histograms, which may be in the form of CDFs as explained above. In embodiments, module 420 may interpolate from a minimal case of four up to a maximal case of thirty two (32) CDFs per color component per camera to obtain a final single contrast-enhanced Lab pixel. The former, minimal case, applies where inter-tile interpolation is bi-linear, and, CDFs are wide (i.e. 256, 512, or even more). The latter, maximal case, applies where inter-tile interpolation is bi-cubic and each of 16 CDFs is in itself a bi-linear interpolation of two adjacent narrow (64 bin) CDFs. For each output Lab pixel, four or sixteen respective tiles may be selected. The Lab pixel may reside in a rectangle formed by center points of the selected four (or sixteen) tiles. In embodiments, the pixel's Lab values feed the LUTs of its respective four (or sixteen) tiles. The final Lab values of the output pixel may be a bi-linear interpolation of the four sets of Lab values (or bi-cubic interpolation of the sixteen sets of Lab values). Thus, module 420 may utilize the Lab values to apply the interpolation algorithm in order to generate contrast-enhanced Lab values, in accordance with the embodiments discussed above. Contrast enhanced Lab pixels are fed to modules 430 that convert them to contrast enhanced YCbCr 4:2:2 10 bit video outputs 440.

Referring again to FIG. 4A, modules 430 may be implemented with successive steps of matrix multiplication and vector addition (MAD) and non-linear functions (implemented as Look-Up Tables, i.e. LUTs). Outputs 440 may subsequently be fed to the next stages of the video pipeline. Formatting output 440 to YCbCr 4:2:2 10 bit may maintain the compatibility between the existing modules within FPGA 402 and may reduce design efforts.

In embodiments, each component within FPGA 402 may include a combination of one or more of the following elements whose properties may vary depending on the FPGA vendor and FPGA family:

1. Look Up Tables (LUTs) for combinational functions. Per such a LUT: 1 bit output as a function of 4-6 bit input.
2. Flip-Flops for sequential operations and registers.
3. Digital Signal Processors (DSPs) i.e. multipliers and adders.
4. Internal 9K-bit memory modules that may be used as, and not limited to be used as, Read Only Memory (ROM) LUTs, Random Access Memory (RAM) LUTs, and First In First Out memories (FIFOs). In embodiments, size of the memory modules may vary with other FPGA families. In an example, 18 bit data output may be generated in response to a 9 bit input address.

Embodiments of the present specification are implemented as firmware, i.e. a logic module instantiated in FPGA 402. The implementation may operate simultaneously on live video from multiple viewing elements, where each video may be processed independently. The embodiments may be implemented in the video processing pipeline between the de-mosaic stage (sensors' DSPs outputs) and the frame grabber input (one of four, used for rescaling, zoom, etc.). The implementation in accordance with various embodiments may be optionally bypassed by activating an FPGA-internal logic switch 480 or by setting clipping thresholds to zero, or by setting interpolator to bypass the CDFs. Following are some of the advantages of using an FPGA implementation in embodiments of the present specification:

1. Reliability. FPGA is a firmware (i.e. hardware) application resulting in reliability in one or more of the following forms:
   - Algorithm can run even when the software crashes. This is beneficial during real-time procedures in clinics.
   - Hardware/firmware is less likely to crash in real-time, than software.
   - Once simulated and tested thoroughly, unexpected failures are less likely to occur, compared with software.
   - The algorithm, as well as all other image processing modules, can start running quickly after system power-up, without having to wait for the much slower software booting. In an embodiment, they can start running within three seconds.
2. Availability. The use of a General Processing Unit (GPU) may be avoided in the system. The GPU may compliment the FPGA but may not replace it. Limitations to using a GPU may include:
   - An extra module that can crash in real-time operation, especially when it relies on software for its operation.
   - Higher BOM cost.
   - Longer system assembly phase.
   - More complex system maintenance.
   - Additional software engineers to program and debug the GPU.
   - Bigger system size.
   - Higher power consumption (approximately 150 W or more, compared with FPGA's approximately 8.5 W in embodiments of the specification). Higher power consumption could imply an extra size and cost of system power supply and higher heat dissipation, requiring a stronger fan resulting in a higher acoustic noise.
3. Complementing the GPU. Even if the system does include a GPU, it is still worthwhile to relieve it from the task of running the algorithm (therefore assigning the task to the FPGA) as the algorithm introduces a heavy computational load on the GPU to the point where it could get in the GPU's way of running other important algorithms such as, for example, pattern recognition, 3D imaging, real-time OSD etc.
4. Architecture. Experience shows that a non-GPU based computer is overwhelmingly under powered for running the algorithm, as the maximal equivalent ingress frame rate it can handle drops dramatically to about ~1-3 per second. In general, the internal architecture of an FPGA that allows performing thousands of tasks simultaneously, in parallel (even at the cost of a slower clock—about ~1/20 of a processor) is more suitable for this type of application.

Figure 5A:
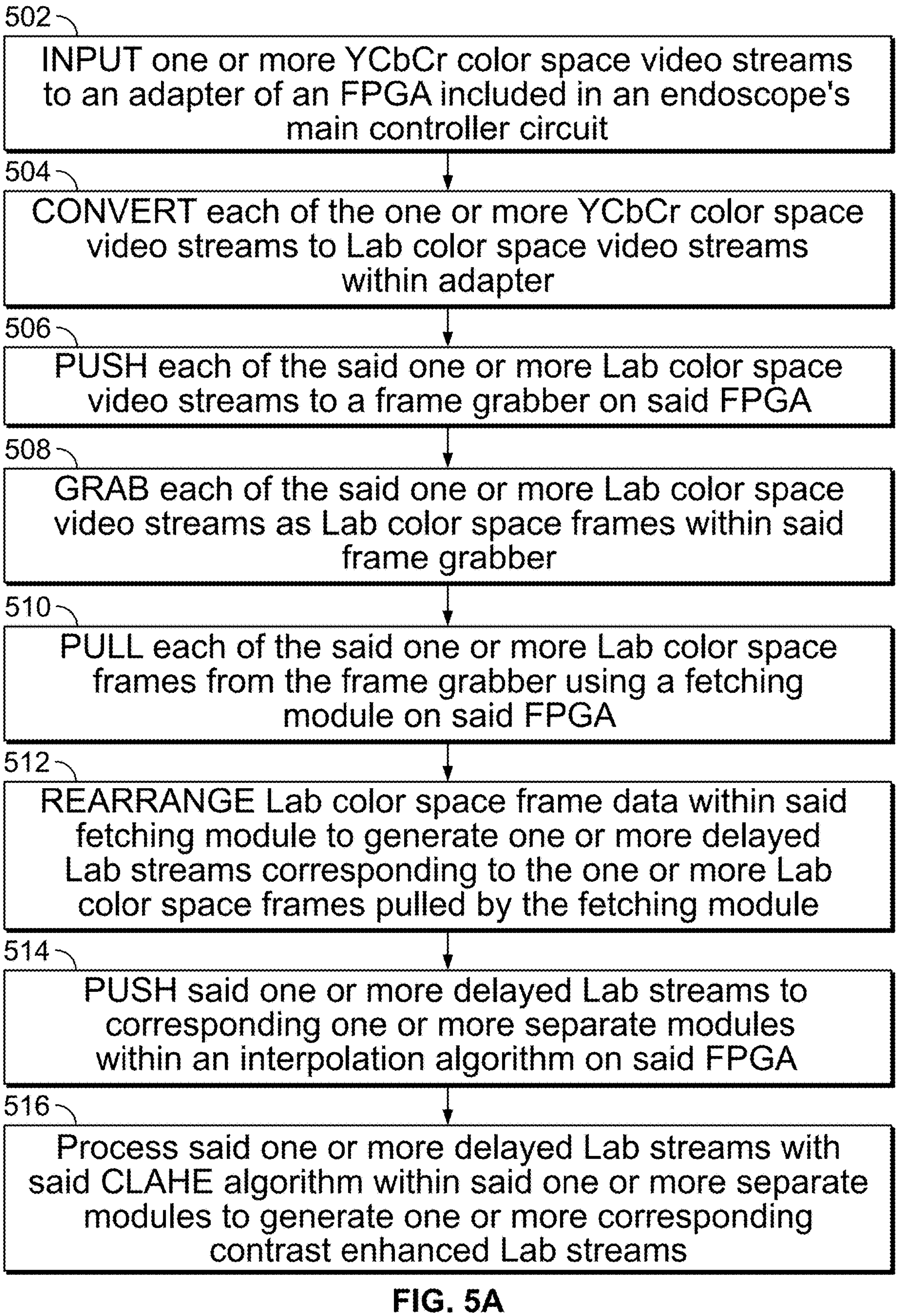
FIG. 5A is a flowchart illustrating the steps of enhancing images obtained by a multiple viewing elements endoscope system using a contrast limited adaptive histogram equalization (CLAHE) algorithm, in accordance with an embodiment of the present specification.

FIG. 5A is a flowchart illustrating the steps of enhancing images obtained by a multiple viewing elements endoscope system using a contrast limited adaptive histogram equalization (CLAHE) algorithm, in accordance with an embodiment of the present specification. At step 502 one or more YCbCr color space video streams each obtained from one or more viewing elements of an endoscope are input to an adapter of an FPGA within the endoscope's main controller circuit. In some embodiments, YCbCr input from each of at least two viewing elements of the endoscope is input to the adapter. In some embodiments, each YCbCr input is 8 bit, 10 bit, or of any other length per component. In one embodiment, the YCbCr input is of 10 bit per component.

At step 504, each of the one or more YCbCr color space video streams are converted to corresponding number of Lab color space video streams within said adapter. In some embodiments, each YCbCr input including 10 bit per color component is converted by the adapter to a 12 bit per component Lab color space video stream, of which all 12 bits are used for the L component, whereas 10 bits are used for each of a and b color components, totaling 32 bits per Lab pixel.

At step 506 each of the said one or more Lab color space video streams are pushed to a frame grabber on said FPGA and at step 508 said one or more Lab color space video streams are grabbed as corresponding one or more Lab color space frames within said frame grabber. In some embodiments, the frame grabber is fed by two Lab color space video streams, each coming from a distinct viewing element of the endoscope.

At step 510 said one or more Lab color space frames are fetched from the frame grabber using a fetching module on said FPGA. The fetching module may keep track of the ingress video frame timing (i.e. line count) and may instruct the frame grabber regarding which rows to fetch from an associated memory device. These rows are calculated from the video lines that may be needed to be displayed, and which are at constant phase shift relative to the ingress frame. At step 512, Lab color space frame data of the one or more Lab color space frames within said fetching module is rearranged to generate one or more delayed Lab streams corresponding to the one or more Lab color space frames pulled by the fetching module. At step 514, said one or more delayed Lab streams are pushed to one or more separate modules within an interpolation algorithm on said FPGA, each delayed Lab stream being fed to a distinct module within the interpolation algorithm. At step 516, the one or more delayed Lab streams are processed with said CLAHE algorithm within said separate modules to generate corresponding on eor more contrast enhanced Lab streams. In various embodiments, data from fetched rows is rearranged by the fetching module to a format understood by the interpolation algorithm. In an embodiment, the data from the fetched rows may include two video streams (one per each viewing element) where each video stream comprises Lab components. The delayed Lab streams, corresponding to each viewing element, are fed to separate modules within the interpolation algorithm where they are similarly processed in accordance with the CLAHE algorithm as described in the present specification.

Figure 5B:
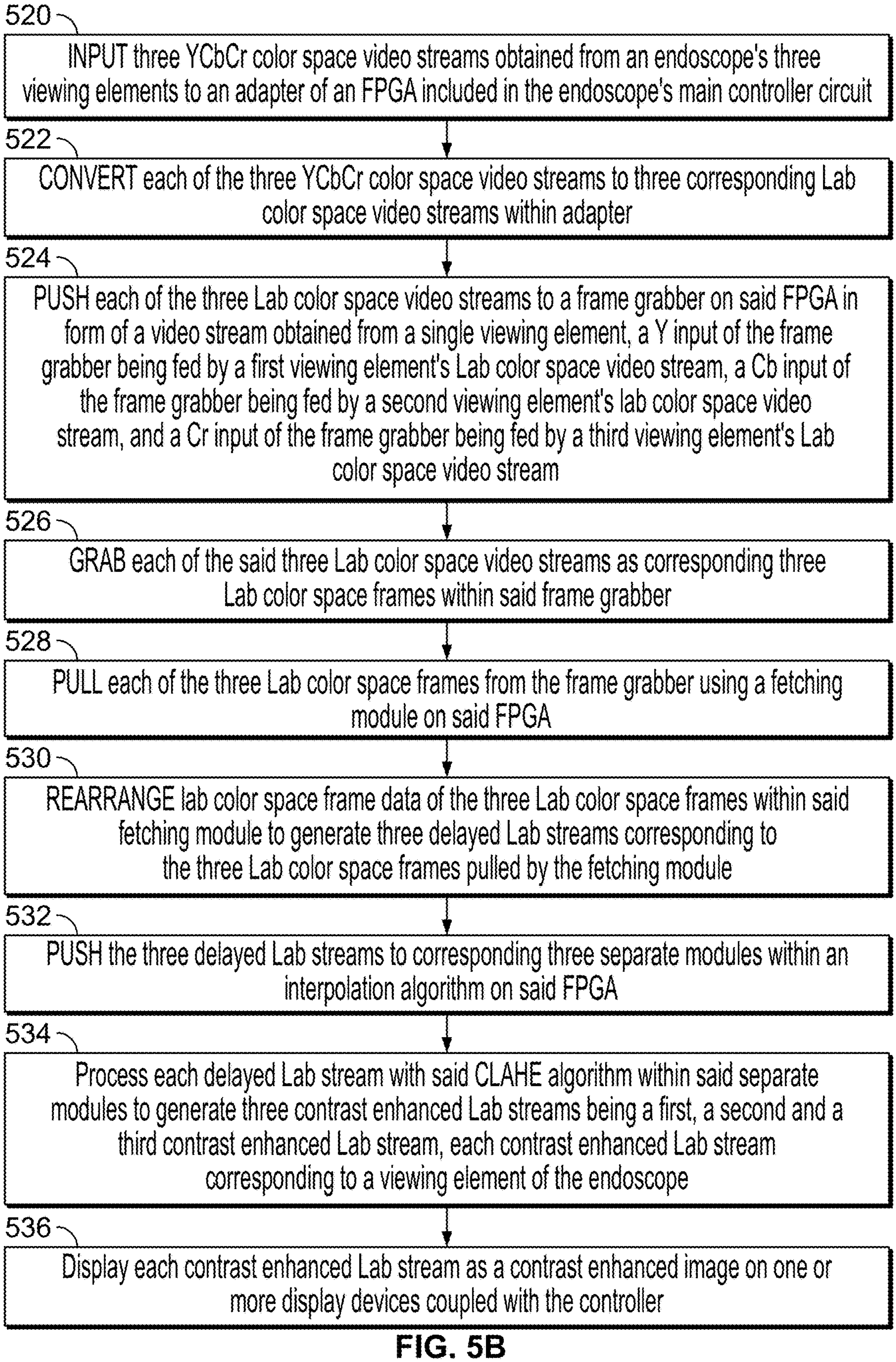
FIG. 5B is a flowchart illustrating the steps of enhancing images obtained by an endoscope system having three viewing elements, by using a contrast limited adaptive histogram equalization (CLAHE) algorithm, in accordance with an embodiment of the present specification.

FIG. 5B is a flowchart illustrating the steps of enhancing images obtained by an endoscope system having three viewing elements, by using a contrast limited adaptive histogram equalization (CLAHE) algorithm, in accordance with an embodiment of the present specification. At step 520 three YCbCr color space video streams, each obtained from one of the three viewing elements of the endoscope, are input to an adapter of an FPGA within the endoscope's main controller circuit. In some embodiments, each YCbCr input is 8 bit, 10 bit, or of any other length per component. In one embodiment, the YCbCr input is of 10 bit per component.

At step 522, each of the three YCbCr color space video streams are converted to three Lab color space video streams respectively within said adapter. In some embodiments, each YCbCr input including 10 bit per color component is converted by the adapter to a 12 bit per component Lab color space video stream, of which all 12 bits are used for the L component, whereas 10 bits are used for each of a and b color components, totaling 32 bits per Lab pixel.

At step 524 each of the three Lab color space video streams are pushed to a frame grabber on said FPGA and at step 526 the three Lab color space video streams are grabbed as corresponding three Lab color space frames within said frame grabber. In some embodiments, the frame grabber's Y input is fed by a left viewing element's Lab, Cb input by a central viewing element's Lab, and Cr input by a right viewing element's Lab—i.e., frame grabber is fed by three viewing elements. This mode of operation may be advantageous in using a single frame grabber (for use with one camera endoscopes in accordance with some embodiments) with a multiple camera endoscope.

At step 528 the three Lab color space frames are fetched from the frame grabber using a fetching module on said FPGA. The fetching module may keep track of the ingress video frame timing (i.e. line count) and may instruct the frame grabber regarding which rows to fetch from an associated memory device. These rows are calculated from the video lines that may be needed to be displayed, and which are at constant phase shift relative to the ingress frame. At step 530, Lab color space frame data of the three Lab color space frames within said fetching module is rearranged to generate three delayed Lab streams, each corresponding to one of the three Lab color space frames pulled by the fetching module. At step 532, the three delayed Lab streams are pushed to three separate modules within an interpolation algorithm on said FPGA, each delayed Lab stream being fed to a distinct module within the interpolation algorithm. At step 534, the three delayed Lab streams are processed with said CLAHE algorithm within said separate modules to generate corresponding three contrast enhanced Lab streams. In various embodiments, data from fetched rows is rearranged by the fetching module to a format understood by the interpolation algorithm. In an embodiment, the data from the fetched rows may include three video streams (one per each viewing element) where each video stream comprises Lab components. The delayed Lab streams, corresponding to each viewing element, are fed to separate modules within the interpolation algorithm where they are similarly processed in accordance with the CLAHE algorithm as described in the present specification. At step 536, each contrast enhanced Lab stream is displayed as a contrast enhanced image on one or more display devices coupled with the controller.

Figure 6A:
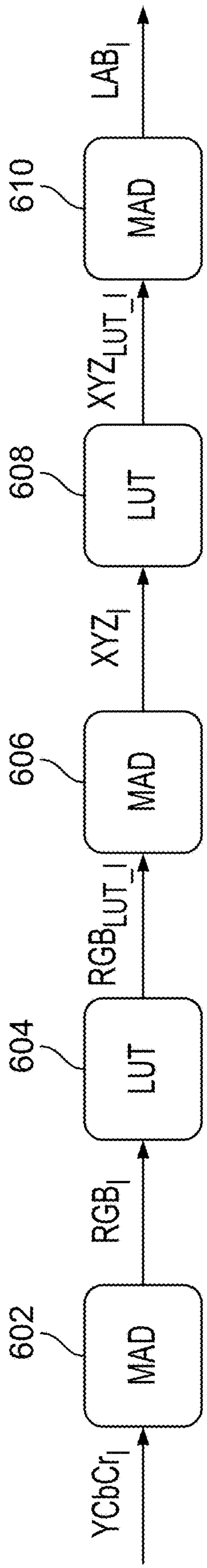
FIG. 6A illustrates a process pipeline that converts YCbCr color space to Lab color space, in accordance with embodiments of the specification.

FIG. 6A illustrates a process pipeline that converts YCbCr color space to Lab color space, in accordance with embodiments of the specification. This is done in the Lab, 10*b* (12*b*, in some embodiments) modules 406 within the adapter 405 shown in FIG. 4A. YCbCr components, or any other color space components, originating from the camera undergo these processes using linear and non-linear operators. In embodiments, the MADs multiply a three-component vector by a designated 3×3 matrix, then add another 3-component designated vector. The matrices and vectors may be unique for each MAD instantiation. Also, in embodiments, LUTs may operate independently and simultaneously on the three components of the input vector, to perform non-linear functions. The non-linear functions may be unique for each LUT instantiation. Within a LUT, the same function may be applied to all three components.

The conversion process of FIG. 6A is illustrated for one camera, and may be explained in five steps. At step 602, a MAD instantiation performs YCbCr to RGB conversion. At 604, a LUT performs a function similar to Y(x)=x^2.40 (Inverse Gamma correction, known to those skilled in the art). At 606, a MAD instantiation performs RGB to XYZ conversion. At 608, a LUT executes a function similar to Y(x)=x^0.33 necessary for the Lab conversion, which is known to those skilled in the art. At 610, a MAD instantiation performs XYZ to Lab conversion excluding the non-linear function, performed already in previous step 608.

Figure 6B:
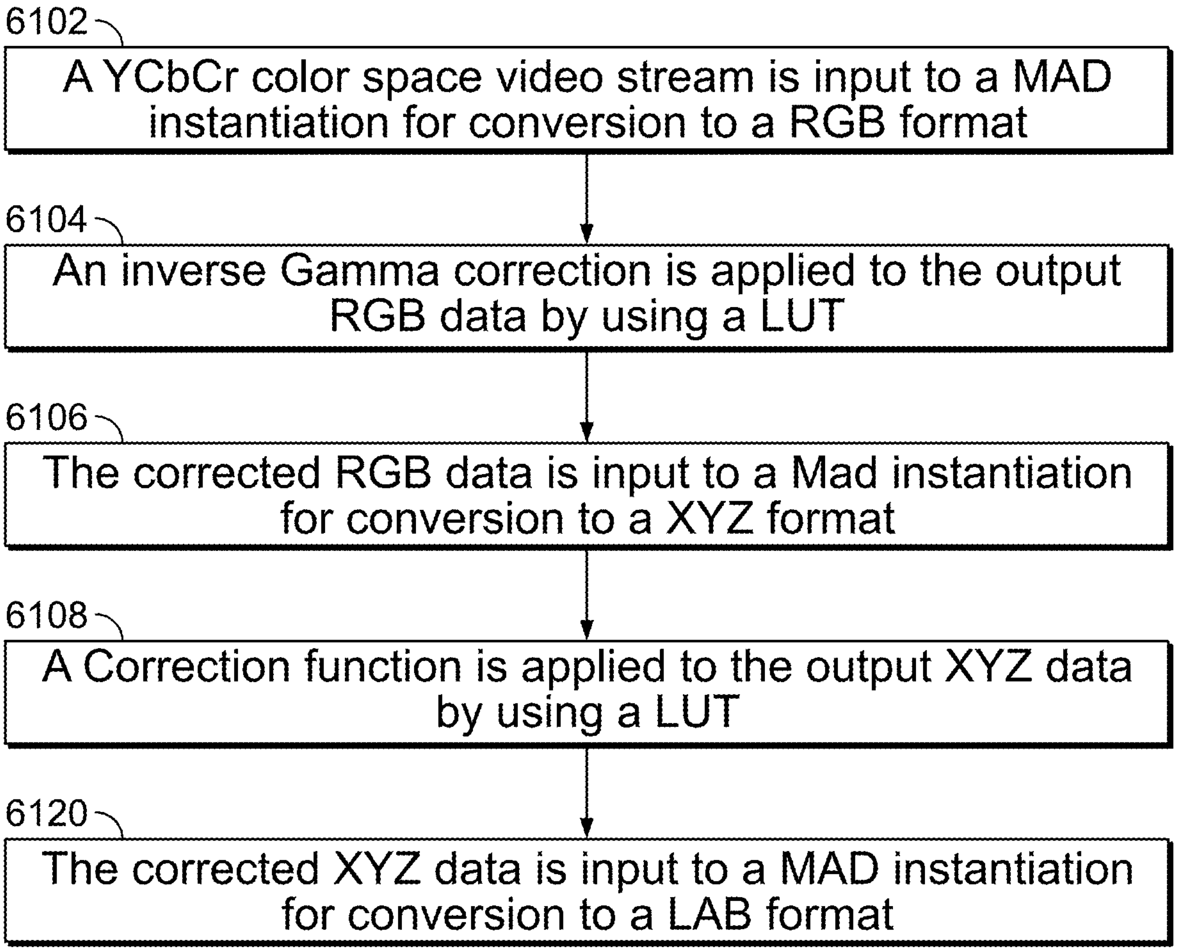
FIG. 6B is a flowchart illustrating the steps performed by the process pipeline shown in FIG. 6A.

FIG. 6B is a flowchart illustrating the steps performed by the process pipeline shown in FIG. 6A. At step 6102 a YCbCr color space video stream is input to a MAD instantiation for conversion to a RGB format. At step 6104 an inverse Gama correction is applied to the output RGB data by using a LUT. In an embodiment, a function similar to Y(x)=x^2.40 is applied to the RGB data. At step 6106, the corrected RGB data output at step 6104 is input to a MAD instantiation for conversion to a XYZ format. At step 6108 a correction function is applied to the output XYZ data by using a LUT. In an embodiment, a function similar to Y(x)=x^0.33 is applied to the XYZ data. At step 6120, the corrected XYZ data output at step 6108 is input to a MAD instantiation and converted to a LAB format.

Figure 7A:
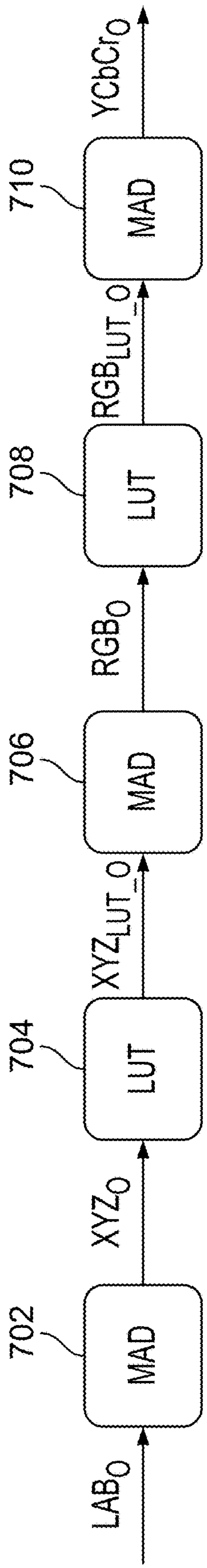
FIG. 7A illustrates a process pipeline that converts Lab color space to YCbCr color space, in accordance with embodiments of the specification.

FIG. 7A illustrates a process pipeline that converts Lab color space to YCbCr (or any other) color space, in accordance with embodiments of the specification. This is done in modules 430 shown in FIG. 4A. The pipeline shown in FIG. 7A is the inverse of the pipeline shown in FIG. 6A. A Lab format may not enable screens to display video images effectively, therefore they are converted back to YCbCr (or any other color space) that may be compatible with one or more displays used with the endoscope system.

The conversion process of FIG. 7A is illustrated for one camera, and may be explained in a plurality of steps, and in one embodiment, five steps. At step 702 a MAD instantiation performs Lab to XYZ conversion excluding the non-linear function, performed in the next step and is known to those skilled in the art. At the next step 704, a LUT executes a function similar to Y(x)=x^3.00. At step 706, a MAD instantiation performs XYZ to RGB conversion. At step 708, a LUT executes a function similar to Y(x)=x^(1/2.40) (Gamma correction). At step 710, a MAD instantiation performs RGB to YCbCr conversion. In some embodiments, modules 430 of FIG. 4A may include a decimator for converting the YCbCr 4:4:4 at the output of step 520, to YCbCr 4:2:2.

Figure 7B:
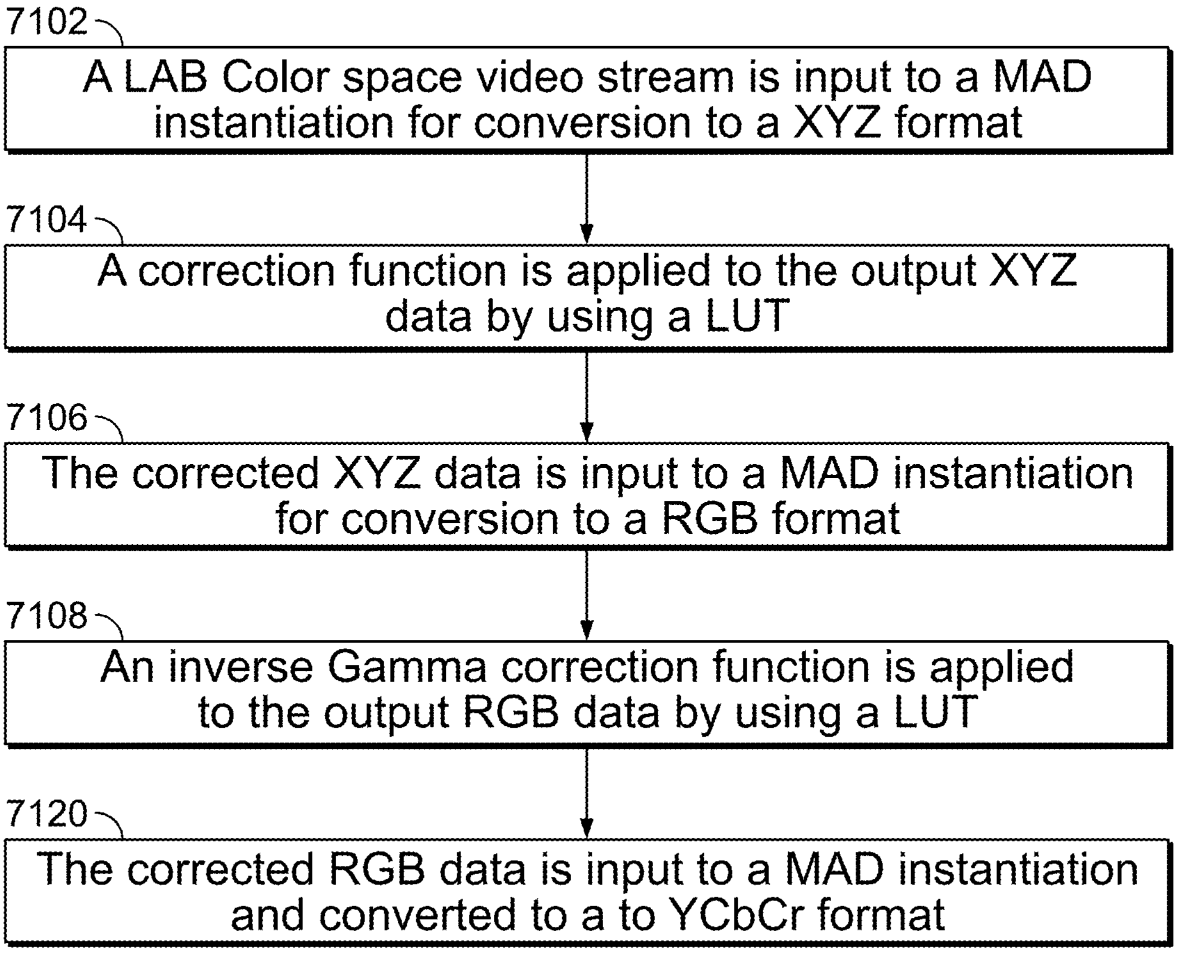
FIG. 7B is a flowchart illustrating the steps performed by the process pipeline shown in FIG. 7A.

FIG. 7B is a flowchart illustrating the steps performed by the process pipeline shown in FIG. 7A. At step 7102 a LAB color space video stream is input to a MAD instantiation for conversion to a XYZ format. At step 7104 a correction function is applied to the output XYZ data by using a LUT. In an embodiment, a function similar to Y(x)=x^3.00 is applied to the XYZ data. At step 7106, the corrected XYZ data output at step 7104 is input to a MAD instantiation for conversion to a RGB format. At step 7108 an inverse Gama correction function is applied to the output RGB data by using a LUT. In an embodiment, a function similar to Y(x)=x^(1/2.40) is applied to the RGB data. At step 7120, the corrected RGB data, output at step 7108 is input to a MAD instantiation and converted to a to YCbCr format.

Figure 8B:
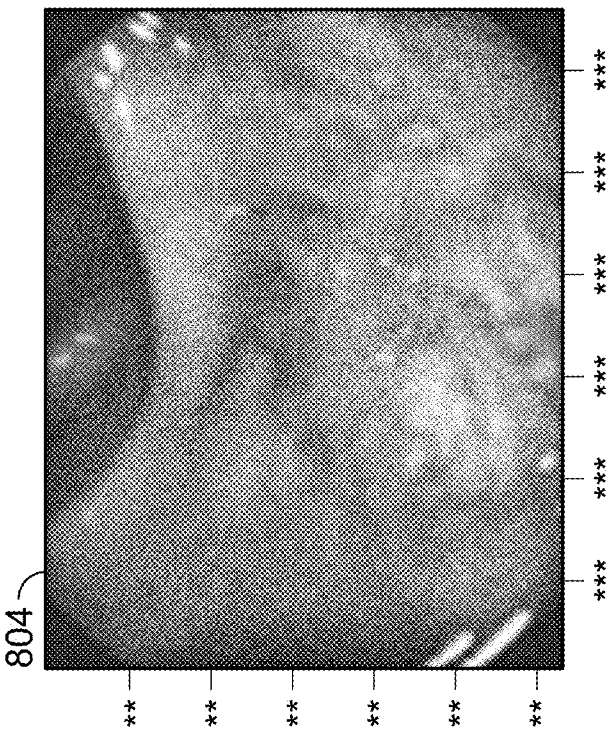
FIG. 8B illustrates the image of FIG. 8A enhanced by using the method of the present specification.
Figure 8A:
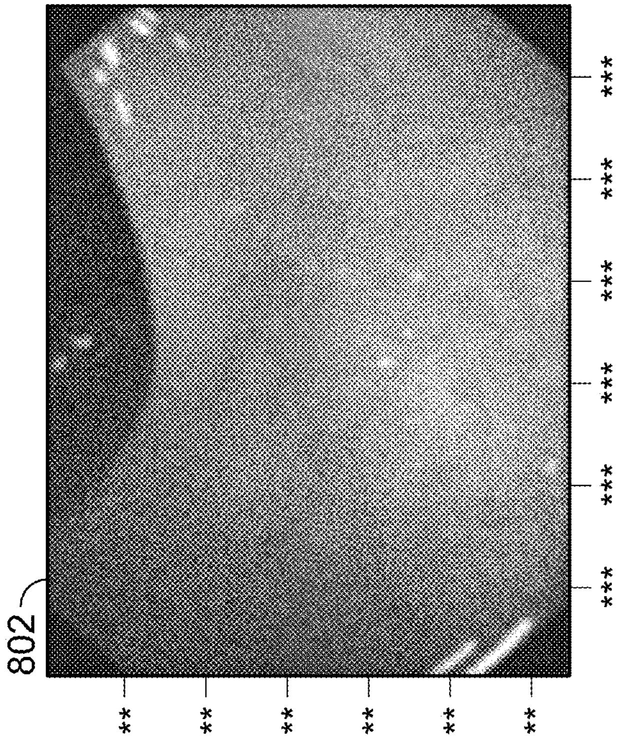
FIG. 8A illustrates a traditional image captured by an endoscope placed inside a body cavity.

FIG. 8A illustrates a traditional image 802 captured by an endoscope placed inside a body cavity. FIG. 8B illustrates the image of FIG. 8A enhanced by using the method of the present specification. Image 804 presents a highly enhanced image as compared to image 802 resulting from user's control over contrast and noise in accordance with the embodiments of the present specification.

Advantages of FPGA firmware implementation for image enhancement were discussed above. Embodiments of the present specification allow image enhancement during real time video capture and display, in addition to enabling image enhancement of still images. Moreover, embodiments of the specification operate on Lab color space, thus allowing greater contrast enhancement abilities. Additionally, tile overlapping, as described in embodiments above further enhance traditional CLAHE implementations. Yet another step for enhancement is the use of bi-cubic interpolation for inter-tile interpolation. The various advantages are applicable simultaneously to videos captured by multiple viewing elements in an endoscope system.

The above examples are merely illustrative of the many applications of the system of present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

We claim:

1. A method of enhancing images obtained by a medical device system using a contrast limited adaptive histogram equalization (CLAHE) process, wherein the medical device system comprises (a) one or more processing boards configured to implement the process, and (b) a medical device operatively coupled to the one or more processing boards, wherein the medical device is configured to be inserted into a body of a patient and includes a first viewing element, the method comprising the steps of:

receiving a YCbCr color space video stream;

converting the YCbCr color space video stream to Lab color space video stream;

building histogram information based on the Lab color space video stream, including splitting the Lab color space video stream into a plurality of tiles, wherein each of the plurality of tiles overlaps with its neighboring tiles;

converting the histogram information into cumulative distribution function values;

obtaining the Lab color space video stream as Lab color space frames;

rearranging the Lab color space frames to generate a delayed Lab stream;

generating an enhanced Lab stream, using the delayed Lab stream and the cumulative distribution function values; and displaying an output video stream indicative of the enhanced Lab stream.

2. The method of claim 1, wherein the YCbCr color space video stream is received by an adapter of the one or more processing boards, the adapter having a conversion module, and wherein the YCbCr color space video stream is converted from the YCbCr color space video stream to the Lab color space video stream by the conversion module.

3. The method of claim 1, wherein splitting the Lab color space video stream into the plurality of tiles includes using bi-cubic interpolation and/or bi-linear interpolation.

4. The method of claim 1, wherein units of tile heights are in video lines and units of tile widths are in pixels.

5. The method of claim 1, wherein the method further comprises the steps of:

performing YCbCr to RGB conversion using MAD instantiation;

performing a function similar to Y(x)=x^2.40 using a LUT;

performing RGB to XYZ conversion using MAD instantiation;

executing a function similar to Y(x)=x^0.33 using a LUT; and performing XYZ to Lab conversion using MAD instantiation.

6. The method of claim 1, wherein the Lab color space frames are obtained using a frame grabber of the one or more processing boards.

7. The method of claim 6, wherein the one or more processing boards comprises a base board module, and wherein the base board module further comprises a random access memory module in communication with the frame grabber.

8. The method of claim 1, wherein the rearranging the Lab color space frames to generate a delayed Lab stream includes using a fetching module of the one or more processing boards.

9. The method of claim 1, further comprising a medical device configured to be inserted into a body of a patient, the medical device including the first viewing element and a second viewing element.

10. A medical device system comprising:

a control unit configured to be operatively coupled to a medical device, wherein the control unit comprises:

one or more processing boards that implement a contrast limited adaptive histogram equalization (CLAHE) algorithm to enhance images obtained by a first viewing element of the medical device, wherein the one or more processing boards perform the steps of:

receiving a first video stream from the first viewing element, building first histogram information based on a first portion of the first video stream, building second histogram information based on a second portion of the first video stream, converting the first histogram information into first cumulative distribution function values, including applying a first clipping threshold to the first histogram information, converting the second histogram information into second cumulative distribution function values, including applying a second clipping threshold to the second histogram information, wherein the second clipping threshold is different from the first clipping threshold, generating a first enhanced video stream based on the first cumulative distribution function values and the second cumulative distribution function values, and sending an output video stream indicative of the first enhanced video stream to a display.

11. The system of claim 10, wherein the one or more processing boards further perform the steps of:

obtaining the first video stream as a first plurality of frames; and rearranging the first plurality of frames to generate a first delayed video stream;

wherein generating the first enhanced video stream includes using the first delayed video stream.

12. The system of claim 10, wherein building first histogram information based on the first video stream includes splitting the first video stream into a first plurality of tiles, wherein units of tile heights are in video lines and units of tile widths are in pixels, and wherein each of the first plurality of tiles overlaps with its neighboring tiles.

13. The system of claim 10, wherein the one or more processing boards further perform the steps of: converting the first video stream from a first color space video stream to a second color space video stream, including the steps of:

performing YCbCr to RGB conversion using MAD instantiation;

performing a function similar to $Y(x)=x^{2.40}$ using a LUT;

performing RGB to XYZ conversion using MAD instantiation;

executing a function similar to $Y(x)=x^{0.33}$ using a LUT; and performing XYZ to Lab conversion using MAD instantiation.

14. The system of claim 10, wherein the one or more processing boards further perform the steps of: converting the first video stream from a first color space video stream to a second color space video stream, including the steps of:

performing Lab to XYZ conversion using MAD instantiation;

executing a function similar to $Y(x)=x^{0.33}$ using a LUT;

performing XYZ to RGB conversion using MAD instantiation;

performing a function similar to $Y(x)=x^{(1/2.40)}$ using a LUT; and performing RGB to YCbCr conversion using MAD instantiation.

15. A non-transient computer readable medium containing program instructions for causing a computer to perform a method of enhancing images obtained by a first viewing element in a medical device system using a contrast limited adaptive histogram equalization (CLAHE) process, wherein said medical device system comprises a processor configured to implement the process, and a medical device operatively coupled to the processor, the medical device being configured for insertion into a body of a patient and including the first viewing element, the method comprising the steps of:

receiving a first video stream from the first viewing element, building first histogram information based on a first portion of the first video stream, building second histogram information based on a second portion of the first video stream, converting the first histogram information into first cumulative distribution function values, including applying a first clipping threshold to the first histogram information, converting the second histogram information into second cumulative distribution function values, including applying a second clipping threshold to the second histogram information, wherein the second clipping threshold is different from the first clipping threshold, generating a first enhanced video stream based on the first cumulative distribution function values and the second cumulative distribution function values, and sending an output video stream indicative of the first enhanced video stream to a display.

16. The computer readable medium of claim 15, the method further comprising:

obtaining the first video stream as a first plurality of frames; and rearranging the first plurality of frames to generate a first delayed video stream;

wherein generating the first enhanced video stream includes using the first delayed video stream.

17. The computer readable medium of claim 15, the method further comprising the step of converting the first video stream from a first color space video stream to a second color space video stream, comprising the steps of:

performing YCbCr to RGB conversion using MAD instantiation;

performing a function similar to $Y(x)=x^{2.40}$ using a LUT;

performing RGB to XYZ conversion using MAD instantiation;

executing a function similar to $Y(x)=x^{0.33}$ using a LUT; and performing XYZ to Lab conversion using MAD instantiation.

18. The computer readable medium of claim 15, the method further comprising converting the first enhanced video stream from a first color space video stream to a second color space video stream.

19. The computer readable medium of claim 18, wherein converting the first enhanced video stream from the first color space video stream to the second color space video stream comprises the steps of:

performing Lab to XYZ conversion using MAD instantiation;

executing a function similar to Y(x)=xˆ0.33 using a LUT;

performing XYZ to RGB conversion using MAD instantiation;

performing a function similar to Y(x)=xˆ(1/2.40) using a LUT; and performing RGB to YCbCr conversion using MAD instantiation.

20. The computer readable medium of claim 15, wherein building first histogram information based on the first video stream includes splitting the first video stream into a first plurality of tiles, wherein units of tile heights are in video lines and units of tile widths are in pixels, and wherein each of the first plurality of tiles overlaps with its neighboring tiles.

* * * * *